United States Patent

Teleha et al.

[11] Patent Number: 5,594,001
[45] Date of Patent: Jan. 14, 1997

[54] POLYCYCLIC SYSTEMS, AND DERIVATIVES THEREOF, AS NEUROTRANSMITTER RELEASE ENHANCERS USEFUL IN THE TREATMENT OF COGNITIVE DISORDERS

[75] Inventors: Christopher A. Teleha; Wendell W. Wilkerson, both of New Castle; Richard A. Earl, Wilmington, all of Del.

[73] Assignee: The DuPont Merck Pharmaceutical Company, Wilmington, Del.

[21] Appl. No.: 216,881

[22] Filed: Mar. 28, 1994

Related U.S. Application Data

[63] Continuation-in-part of Ser. No. 44,012, Apr. 8, 1993, abandoned.

[51] Int. Cl.$^6$ .................. A61K 31/435; A61K 31/44; C07D 491/052; C07D 221/08
[52] U.S. Cl. .................. 514/290; 514/291; 514/332; 514/333; 546/89; 546/101; 546/111; 546/255; 546/256; 546/267
[58] Field of Search ............... 546/89, 111, 255, 546/256, 267, 101; 514/290, 291, 332, 333

[56] References Cited

U.S. PATENT DOCUMENTS 4,760,083  7/1988  Myers et al. ............... 514/333
5,173,489  12/1992  Earl et al. ............... 514/252
5,185,447  2/1993  Crapps ............... 546/111

FOREIGN PATENT DOCUMENTS

WO9314085  1/1992  WIPO.
WO9314092  1/1992  WIPO.

OTHER PUBLICATIONS

DeNoble, et al., *Pharmacol. Biochem. Behavior*, (1990) 36:957.
Cook, et al., *Drug Development Research* (1990) 19: 301.
Nickolson, et al., *Drug Development Research* (1990) 19: 285.

*Primary Examiner*—Bernard Dentz
*Attorney, Agent, or Firm*—Karen H. Kondrad; David H. Vance

[57] ABSTRACT

Compounds of Formula (I) have been shown to enhance the release of the neurotransmitter acetylcholine, and thus may be useful in the treatment of diseases of man where subnormal levels of this neurochemical are found, such as in Alzheimer's disease, and other conditions involving learning and cognition. This invention describes compounds, pharmaceutical compositions and methods of treatment comprising compounds of Formula (I):

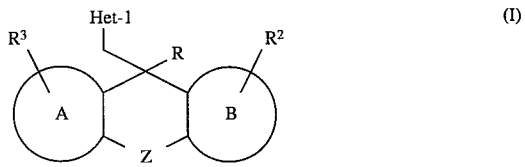

51 Claims, 2 Drawing Sheets

POLYCYCLIC SYSTEMS, AND DERIVATIVES THEREOF, AS NEUROTRANSMITTER RELEASE ENHANCERS USEFUL IN THE TREATMENT OF COGNITIVE DISORDERS

CROSS-REFERENCE TO EARLIER FILED APPLICATIONS

This application is a continuation-in-part of U.S. patent application Ser. No. 08/044,012, filed Apr. 8, 1993 now abandoned. The disclosure of this earlier filed application is hereby incorporated herein by reference.

FIELD OF INVENTION

This invention relates to disubstituted polycyclic compounds, derivatives thereof, pharmaceutical compositions, and methods of use in mammals to treat cognitive disorders and/or neurological dysfunction and/or mood disturbances such as, but not limited to degenerative nervous system diseases. Additionally, these compounds can be used as reagents in studies on the biochemical mechanism of neurotransmitter based diseases.

BACKGROUND OF THE INVENTION

Increasingly there is a need for effective treatments for nervous system disorders and neurological deficiencies. Many of these diseases correlate with increasing age, due mainly to degenerative changes in the nervous systems. Although in early stages of some diseases certain systems are rather specifically affected (e.g. cholinergic systems in Alzheimer's Disease and Myasthenia Gravis, the dopaminergic system in Parkinson's Disease, etc.), multiple neurotransmitter system deficiencies (acetylcholine, dopamine, norepinephrine, serotonin) are generally found at later stages of disease such as senile dementia, multi-infarct dementia, Huntington's Disease, mental retardation, etc. This explains the generally observed multiple symptomatology that includes cognitive, neurological, and effective/psychotic components (see Gottfries, *Psychopharmacol.*, (1985) 86: 245). Deficits in the synthesis and release of acetylcholine in the brain are generally thought to be related to cognitive impairment (see Francis, et al., *N. Engl. J. Med.,* (1985) 7: 313) whereas neurological deficits (e.g., Parkinsonian symptoms) and mood/mental changes may be related to impairment of dopaminergic and serotonergic systems, respectively. Other neurological deficits (e.g. Myasthenia Gravis) are related to cholinergic deficiencies in the peripheral nervous system.

Treatment strategies employed previously encompass vasoactive drugs like vincamine and pentoxifylline; metabolic enhancers like ergoloid mesylates, piracetam, and naftidrofuryl; neurotransmitter precursors like 1-DOPA, choline, and 5-hydroxytryptamine; transmitter metabolizing enzyme inhibitors such as physostigmine; and neuropeptides like adrenocorticotropic hormone and vasopressin-related peptides. Except for L-DOPA treatment for Parkinson's Disease and cholinesterase inhibitor treatment for Myasthenia Gravis, these treatment strategies have generally failed to enhance the residual function of the affected systems by enhancing the stimulus-induced release of neurotransmitters. Theoretically, such an enhancement would improve the signal-to noise ratio during chemical transmission of information, thereby reducing deficits in processes related to cognition, neurological function, and mood regulation.

DeNoble, et al., *Pharmacol. Biochem. Behavior,* (1990) 36: 957; Cook, et al., *Pharmacol. Biochem. Behavior,* (1990) 19: 301; Nickolson, et al., *Pharmacol. Biochem. Behavior,* (1990) 19: 285; and U.S. Pat. No. 4,760,083 (1988), all have shown by in vitro testing that the compound 3,3-bis-(4-pyridinylmethyl)-1-phenylindolin-2-one is useful in the treatment of cognition dysfunction.

U.S. Pat. No. 5,173,489 issued Dec. 22, 1992 discloses α,α'-disubstituted aromatic or heteroaromatic compounds of the formula:

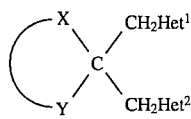

or a salt thereof:

wherein X and Y are taken together to form a saturated ring or unsaturated carbocyclic or heterocyclic first ring and the shown carbon in said ring is α to at least one additional aromatic ring or heteroaromatic ring fused to the first ring; one of Het$^1$ or Het$^2$ is 2, 3, or 4-pyridinyl; or 2,4 or 5-pyrimidinyl, and the other is selected from
(a) 2, 3, or 4-pyridinyl
(b) 2, 4, or 5-pyrimidinyl
(c) 2-pyrazinyl
(d) 3 or 4-pyridazinyl
(e) 3 or 4-pyrazolyl
(f) 2 or 3 tetrahydrofuranyl, and
(g) 3-thienyl which are useful as cognition enhancers. The above references claim the necessity of two heteroaryl pendant groups for activity.

European Patent Application, WO93/14085, published Jul. 22, 1993 discloses compounds of the formula:

where Q is

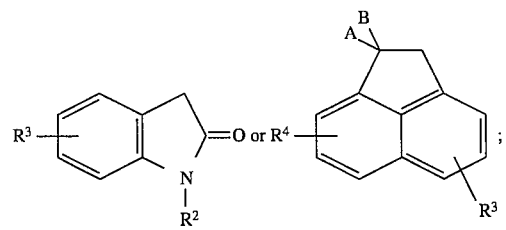

which are useful as neurotransmitter release enhacers.

European Patent Application, WO93/14092, published Jul. 22, 1993, discloses compounds of the formula:

where Q is

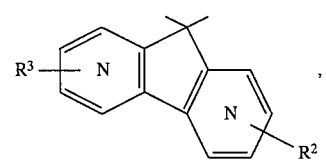

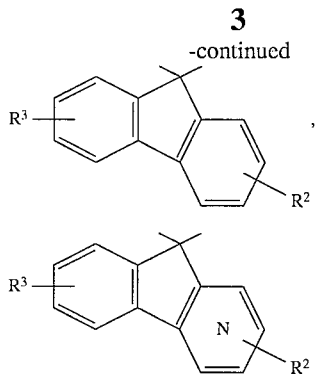

which are useful as neurotransmitter release enhancers.

None of the above references teach or suggest the compounds of the present invention having fused polycyclic systems of the 6-5-5 variety where A is a six-membered aromatic system; B is a five-membered heterocyclic system and C is a five-membered ring between ring systems A and B. In addition, it has been further demonstrated that certain compounds of the present invention, particularly those bearing a 2-fluoropyridinylmethyl group as a substituent on the polycyclic ring system, have the ability to produce a measurable increase in the level of acetylcholine in the brain. This demonstrated ability to produce increases in acetylcholine levels meaurable directly in the brain constitutes a clear and unexpected advantage over compounds previously described in the art.

SUMMARY OF THE INVENTION

It has been found that certain polycyclic compounds enhance the stimulus-induced release of neurotransmitters, specifically acetylcholine, in nervous tissues; thus improving processes involved in learning and memorization of an active avoidance task. Further evidence of this effect is characterized by measurable increases in brain neurotransmitter acetylcholine levels.

Accordingly, there is provided by this invention a class of novel compounds represented by Formula (I) below:

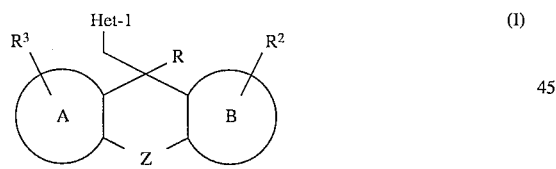

or a pharmaceutically acceptable salt or prodrug thereof wherein:

A is an aromatic or heteroaromatic ring selected from the group consisting of:

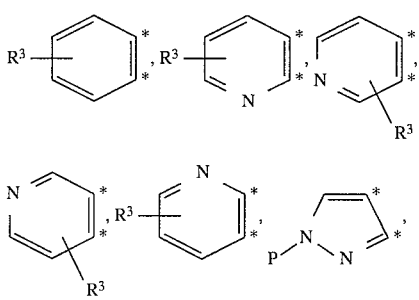

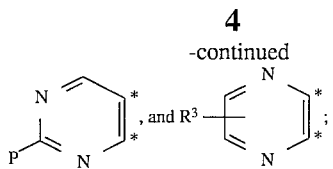

B is an aromatic or heteroaromatic ring selected from the group consisting of:

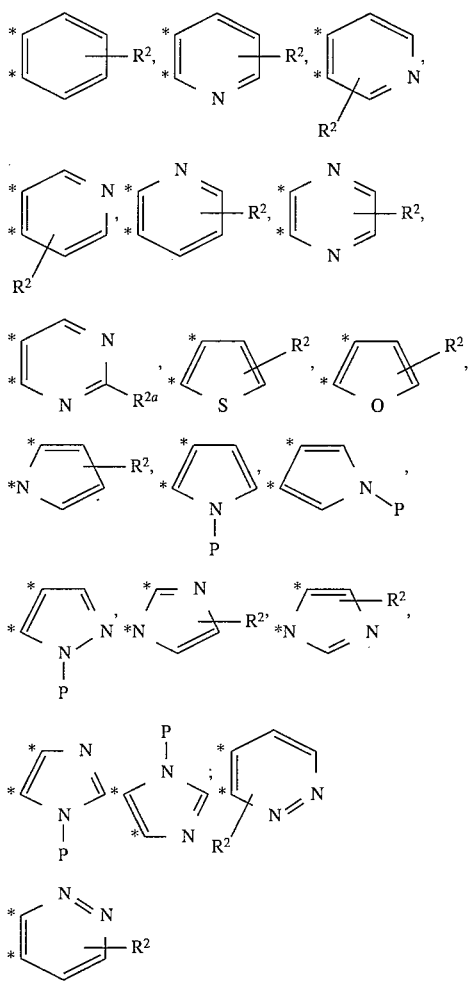

and

Z is a bond, —C(=O)—, —O—, —NP—, —S—, —S(=O)— or —SO$_2$—;

P is H, phenyl, C$_1$–C$_4$ alkyl or benzyl

R$^2$ and R$^3$ are independently H, F, Cl, Br, I, CF$_3$, OH, R$^4$, —(CH$_2$)$_n$C≡CR$^5$, —OR$^4$, NR$^6$R$^{6a}$, —CO$_2$R$^4$, —COR$^4$, —CONH$_2$, —CONHR$^4$, —CONR$^4$R$^{4a}$, —CH$_2$)$_n$NR$^6$COR$^4$ or —S(O)$_m$R$^4$;

R$^{2a}$ is H, C$_1$–C$_4$ alkyl or phenyl;

m is 0, 1, or 2;

R$^4$ and R$^{4a}$ are independently alkyl of 1 to 4 carbons;

Each of Het-1 and Het-2 is independently a heterocycle selected from the group consisting of:

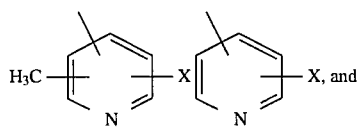

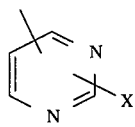

Each X is independently H, F, Cl, Br, I, $CF_3$, $OR^4$, $NR^6R^{6a}$, $NO_2$, or CN R is selected from the group consisting of:
H, —$CH_2$-Phe-W, —$CH_2$-(Het-2), —$(CH_2)_n$—O—$COR^5$, —$(CH_2)_n$—CH=CH—$R^5$, —$(CH_2)_n$—C≡C—$R^5$, —$(CH_2)_n$—Y;

W is H, F, Cl, Br, —CN, $CO_2R^5$, $R^4$, $OR^4$, $S(O)_m$—$R^4$;

Y is —$OR^6$, $NHR^6$, $NR^6R^{6a}$, $NHCOR^6$, $NHCO_2R^6$, $CO_2R^6$, —CN, $CONHR^6$, $CONR^6R^{6a}$, —$COR^6$, —$CH_2$—CH=$CHCO_2R^6$, —$OCOR^6$, or $CO_2Bz$; and n is 1 to 5;

$R^5$, $R^6$ and $R^{6a}$ are independently H or alkyl of 1 to 6 carbons.

Provided that when A is a 6-membered aromatic or heteroaromatic ring, Het-1 and Het-2 are not both selected from

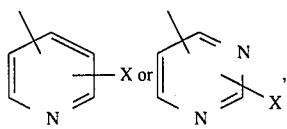

when X is H.

Preferred compounds of the present invention are compounds of Formula (I) or a pharmaceutically acceptable salt or prodrug form thereof wherein:

A is an aromatic or heteroaromatic ring selected from the group consisting of:

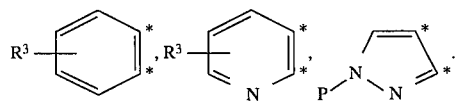

Further preferred compounds of this invention are compounds of the Formula (I) or a pharmaceutically acceptable salt or prodrug form thereof wherein:

A is an aromatic or heteroaromatic ring selected from the group consisting of:

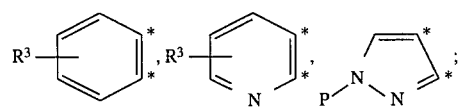

B is an aromatic or heteroaromatic ring selected from the group consisting of:

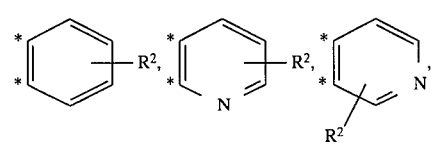

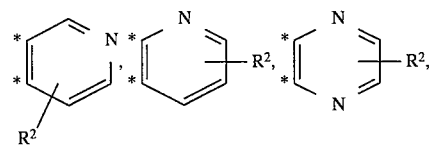

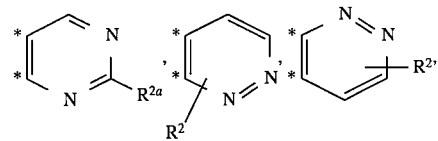

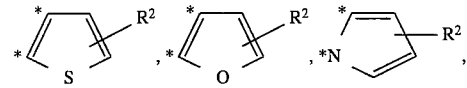

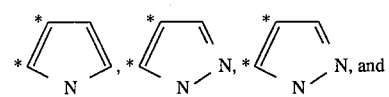

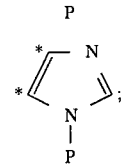

Most preferred compounds of the present invention are compounds of Formula (I) or a pharmaceutically acceptable salt or prodrug form thereof wherein:

A is a six member aromatic or heteroaromatic ring selected from the group consisting of:

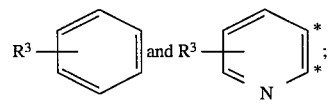

B is an aromatic or heteroaromatic ring selected from the group consisting of:

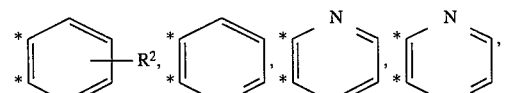

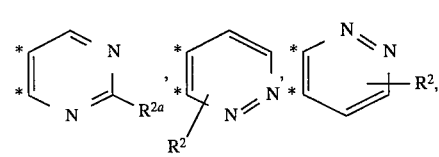

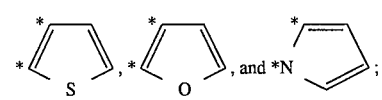

$R^2$ is H, I, $R^4$, —C≡CH, —$OR^4$, —$NR^6R^{6a}$, —$CO_2R^4$, or —$(CH_2)_nNR^6COR^4$;

$R^3$ is H;

Het-1 and Het-2 are independently

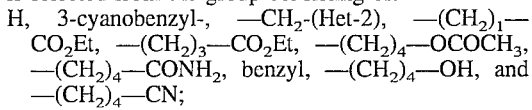

X is H, F, Cl, Br, or OR$^4$;

R is selected from the group consisting of:
H, 3-cyanobenzyl-, —CH$_2$-(Het-2), —(CH$_2$)$_1$—CO$_2$Et, —(CH$_2$)$_3$—CO$_2$Et, —(CH$_2$)$_4$—OCOCH$_3$, —(CH$_2$)$_4$—CONH$_2$, benzyl, —(CH$_2$)$_4$—OH, and —(CH$_2$)$_4$—CN;

Specifically preferred compounds of the present invention are selected from:

(a) 4-(4-Pyridinylmethyl)-4H-indeno[1,2-B]thiophene;
(b) 4-(4-Pyridinylmethyl)-4H-indeno[1,2-B]thiophene-4-pentanenitrile Hydrobromide Hydrate;
(c) 4-(4-Pyridinylmethyl)-4H-indeno[1,2-B]thiophene-4-acetic acid Ethyl Ester Hydrochloride;
(d) 4-(4-Pyridinylmethyl)-4H-indeno[1,2-B]thiophene-4-butanol Acetate (Ester) Hydrochloride;
(e) 4-(4-Pyridinylmethyl)-4H-indeno[1,2-B]thiophene-4-pentanamide Hydrochloride Hydrate;
(f) 2-Fluoro-4-[4-(4-pyridinylmethyl)-4H-indeno[1,2-B]thiophen-4-ylmethyl]-pyridine;
(g) 4-[4-(Phenyl)-4H-indeno[1,2-B]thiophen-4-ylmethyl]-pyridine;
(h) 4-(4-Pyridinylmethyl)-4H-indeno[1,2-B]thiophene-4-butanol;
(i) 4-(4-Pyridinylmethyl)-4H-thieno[2',3':3,4]cyclopenta[1,2-B]pyridine;
(j) 4-[(2-Fluoro-4-pyridinyl)methyl]-4-(4-pyridinylmethyl)-4H-thieno[3',2':4,5]cyclopenta[1,2-B]pyridine;
(k) 1,4-Dihydro-1-(phenylmethyl)-4,4-bis(4-pyridinylmethyl)-indeno[1,2-C]pyrazole; and
(l) 2,4-Dihydro-2-phenyl-4,4-bis(4-pyridinylmethyl)pyrazolo[4,3-B]pyrrolizine.
(m) 9,9-Bis((2-fluoro-4-pyridinyl)methyl)-2-hydroxy-9H-fluorene;
(n) 5-(2-Fluoro-4-pyridinyl)methyl)-5-(4-pyridinylmethyl)-5H-indeno[1,2-b]pyridine;
(o) 5-(2-Fluoro-4-pyridinyl)methyl)-5-(4-pyridinylmethyl)-5H-indeno[2,1-b]pyridine;
(p) 10,10-Bis((2-fluoro-4-pyridinyl)methyl)-9(10H)-anthracenone;
(q) 9-((2-Fluoro-4-pyridinyl)methyl)-9-(4-pyridinylmethyl)-9H-xanthene;
(r) 10-((2-Fluoro-4-pyridinyl)methyl)-10-(4-pyridinylmethyl)-9(10H)-anthracenone;
(s) 9,9-Bis((2-fluoro-4-pyridinyl)methyl)-4-azaxanthene;
(t) 5,5-Bis((2-fluoro-4-pyridinyl)methyl)-5H-indeno[1,2-b]pyridine;
(u) 4,4-Bis((2-fluoro-4-pyridinyl)methyl)-4H-thieno[3',2':4,5]cyclopenta[1,2-b]pyridine;
(v) 9-((2-Fluoro-4-pyridinyl)methyl)-9-(4-pyridinylmethyl)-4-azaxanthene;
(w) 9,9-Bis((2-fluoro-4-pyridinyl)methyl)-2-methoxyfluorene;
(x) 9,9-Bis((2-fluoro-4-pyridinyl)methyl)-7-methoxy-4-azaxanthene;
(y) 10,10-Bis((2-fluoro-4-pyridinyl)methyl)-3-hydroxy-9(10H)-anthracenone;
(z) 10,10-Bis((2-fluoro-4-pyridinyl)methyl)-2,6-dimethoxy-9(10H)-anthracenone;
(aa) 9,9-Bis((2-fluoro-4-pyridinyl)methyl)-cyclopenta[1,2-b:3,4-b']dipyridine;
(bb) 5,5-Bis((2-fluoro-4-pyridinyl)methyl)-2-phenyl-5H-indeno[1,2-d]pyrimidine;
(cc) 10,10-Bis((2-fluoro-4-pyridinyl)methyl)-3-methoxy-9(10H)-anthracenone;
(dd) 9,9-Bis((2-fluoro-4-pyridinyl)methyl)-9H-indeno[2,1-b]pyridine;
(ee) 5,5-Bis((2-fluoro-4-pyridinyl)methyl)-7-(ethynyl)-5H-indeno-[1,2-b]pyridine;
(ff) 9,9-Bis((2-fluoro-4-pyridinyl)methyl)-9H-indeno-[1,2-b]pyrazine;
(gg) 5,5-Bis((2-fluoro-4-pyridinyl)methyl)-5H-indeno-[1,2-d]pyrimidine;
(hh) 5,5-Bis((2-bromo-4-pyridinyl)methyl)-5H-indeno-[1,2-b]pyridine;
(ii) 9,9-Bis((2-fluoro-4-pyridinyl)methyl)-2-((N-methylamino)methyl)fluorene;
(jj) 9,9-Bis((2-fluoro-4-pyridinyl)methyl)-2-((N-methyl-N-methoxycarbonylamino)methyl)fluorene;
(kk) 9,9-Bis((2-fluoro-4-pyridinyl)methyl)-2-((N-methyl-N-acetylamino)methyl)fluorene;
(ll) 10,10-Bis((2-bromo-4-pyridinyl)methyl)-9(10H)-anthracenone;
(mm) 5,5-Bis((2-chloro-4-pyridinyl)methyl)-5H-indeno-[1,2-b]pyridine;
(nn) 5,5-Bis((2-fluoro-4-pyridinyl)methyl)-2-methyl-5H-indeno-[1,2-d]pyrimidine;
(oo) 5,5-Bis((2-methoxy-4-pyridinyl)methyl)-5H-indeno-[1,2-b]pyridine;
(pp) 5,5-Bis((2-fluoro-4-pyridinyl)methyl)-7-(ethyl)-5H-indeno-[1,2-b]pyridine;
(qq) 5,5-Bis((2-chloro-6-methyl-4-pyridinyl)methyl)-5H-indeno-[1,2-b]pyridine;
(rr) 5,5-Bis((2-methyl-4-pyridinyl)methyl)-5H-indeno-[1,2-b]pyridine;
(ss) 5,5-Bis((2-fluoro-4-pyridinyl)methyl)-7-(iodo)-5H-indeno-[1,2-b]pyridine;
(tt) 9,9-Bis((2-fluoro-4-pyridinyl)methyl)-9H-fluorene-1-carboxylic acid, methyl ester;
(uu) 9-((2-Fluoro-4-pyridinyl)methyl)-9-(4-pyridinylmethyl)-9H-fluorene-1-carboxylic acid, methyl ester, racemic;
(vv) 9,9-Bis((2-fluoro-4-pyridinyl)methyl)-9H-fluoren-1-amine;
(ww) 5,5-Bis((2-fluoro-4-pyridinyl)methyl)-5H-cyclopenta[2,1-b:3,4-b']dipyridine;
(xx) 5-((2-Fluoro-4-pyridinyl)methyl)-5-(4-pyridinylmethyl)-5H-cyclopenta[2,1-b:3,4-b']dipyridine-4-carboxylic acid, methyl ester, dihydrochloride salt (racemic);
(yy) 5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (−)-isomer;
(zz) 5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (+)-isomer;
(ab) 5,5-Bis((6-fluoro-3-pyridinyl)methyl)-5H-cyclopenta[2,1-b:3,4-b']dipyridine;

(ac) 5-((6-Fluoro-2-pyridinyl)methyl)-5-(4-pyridinylmethyl)-5H-cyclopenta[2,1-b:3,4-b']dipyridine;

(ad) 5,5-Bis((6-fluoro-2-pyridinyl)methyl)-5H-cyclopenta[2,1-b:3,4-b']dipyridine;

(ae) 5,5-Bis((3-methyl-4-pyridinyl)methyl)-5H-cyclopenta[2,1-b:3,4-b']dipyridine, trihydrochloride salt;

(af) 2-Fluoro-4-((9-(4-pyridinylmethyl)-9H-fluoren-9-yl)methyl)pyridine, hydrochloride salt;

(ag) 5-((2-Fluoro-4-pyridinyl)methyl)-5-(4-pyridinylmethyl)-5H-cyclopenta[2,1-b:3,4b']dipyridine;

(ah) 5,5-Bis((2-fluoro-4-pyridinyl)methyl)thioxanthene-10,10-dioxide;

(ai) 5,5-Bis((2-fluoro-4-pyridinyl)methyl)thioxanthene-10-oxide;

(aj) 2,6-Dimethyl-4-((9-(4-pyridinylmethyl)-9H-fluoren-9-yl)methyl)pyridine, dihydrochloride salt;

(ak) 5-((2,6-Dimethyl-4-pyridinyl)methyl)-5-(4-pyridinylmethyl)-5H-cyclopenta[2,1-b:3,4-b']dipyridine;

(al) 5,5-Bis((2,6-dimethyl-4-pyridinyl)methyl)-5H-cyclopenta[2,1-b:3,4-b']dipyridine, E-2-butendiaote salt.

Also provided are methods for the treatment of cognitive disorders and/or neurological function deficits and/or mood and mental disturbances in patients suffering from nervous system disorders such as Alzheimer's disease, Parkinson's disease, senile-dementia, multi-infarct dementia, Huntington's disease, mental retardation, Myasthenia Gravis, etc., by administering to the host suffering from such disorder a therapeutically effective amount of a compound of Formula (1). The present invention also provides pharmaceutical compositions comprising a therapeutically effective amount of a compound of Formula (I).

The compounds herein described may have asymmetric centers. All chiral, diastereomeric and racemic forms are included in the present invention. Many geometric isomers of olefins, C=N double bonds, and the like can also be present in the compounds described herein, and all such stable isomers are contemplated in the present invention.

When any variable (for example, $R^1$ through $R^6$, m, n, P, W, Y, A, B, etc.) occurs more than one time in any constituent or in formula (I), or any other formula herein, its definition on each occurrence is independent of its definition at every other occurrence. Also, combinations of substituents and/or variables are permissible only if such combinations result in stable compounds.

As used herein and in the claims, "*" denotes the point of attachment of the A ring and B ring to more clearly specify the regioisomers intended.

As used herein and in the claims, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like. "Halo" as used herein and in the claims refers to fluoro, chloro, bromo and iodo; and "counter-ion" is used to represent a small, negatively charged species such as chloride, bromide, hydroxide, acetate, sulfate and the like.

As used herein and in the claims, "aryl" or "aromatic ring" is intended to mean phenyl or naphthyl; "carbocyclic" is intended to mean any stable 5- to 7-membered monocyclic or bicyclic or 7- to 14-membered bicyclic or tricyclic carbon ring, any of which may be saturated, partially unsaturated, or aromatic, for example indanyl, naphthyl, or tetrahydronaphthyl (tetralin).

As used herein and in the claims, the terms "heteroaromatic ring" and "heteroaromatic system" are intended to mean a stable 5- to 6-membered monocyclic or 8- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridinyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl.

The term "substituted", as used herein and in the claims, means that any one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein and in the claims, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., (1985), p. 1418, the disclosure of which is hereby incorporated by reference.

The term "pharmaceutical composition" as used herein and in the claims refers to a composition comprised of a compound and a pharmaceutical carrier selected on the basis of the chosen route of administration and standard pharmaceutical practice.

The term "therapeutically effective" as used herein and in the claims refers to that amount of a compound of formula (I) necessary to enhance the residual function of the affected systems by enhancing the stimulus-induced release of neurotransmitters thereby reducing deficits in processes related to cognition, neurological function, and mood regulation.

The use of "therapeutically effective amount" herein and in the claims is intended to mean that amount useful for the treatment of cognitive disorders and/or neurological function deficits and/or mood and mental disturbances in patients suffering from nervous system disorders such as Alzheimer's disease, Parkinson's disease, senile-dementia, multi-infarct dementia, Huntington's disease, mental retardation, Myasthenia Gravis, etc. Additionally, these compounds can be used as reagents in studies on the biochemical mechanism of neurotransmitter based diseases.

DETAILED DESCRIPTION OF THE INVENTION

Figure 1:
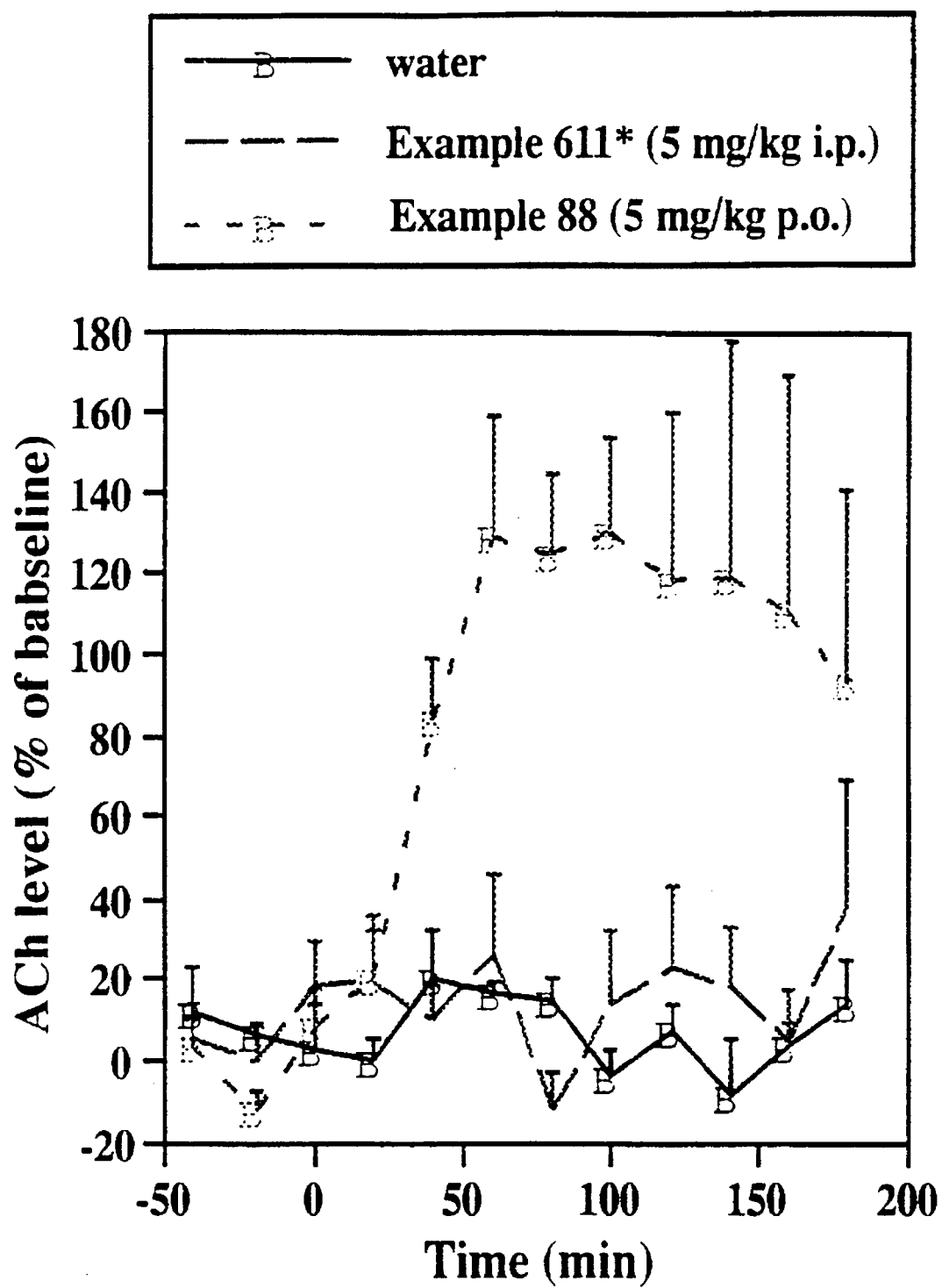

The compounds of this invention can be described as being composed of two parts: the 'core group', that being the tricyclic ring system formed by A and B and the central five- and six-membered ring (C); and the 'pendant groups' that are composed of 'CH$_2$-Het-1' and 'R'.

The cores can be synthesized by the methods described below and in the following references which are hereby incorporated by reference: Laschtuvka, E. and Huisgen, R, *Chem. Ber.,* (1960) 93: 81; Mazzola, V. J., et al., *J. Org. Chem.,* (1967) 32: 486; Rault, S. et al., *Heterocycles,* (1983) 20: 477; Laduree, D. and Robba, M., *Heterocycles,* (1984) 22: 303; Massa, S. et al., *J. Heterocyclic Chem.,* (1990) 27: 1805; and Shen, J.-K. and Katayama, H.; *Chem. Lett.,* (1992) 451.

Additional "core groups" useful for the synthesis of the compounds present invention can be prepared according to methods described in the literature references below, or by an analogous method to that reported:

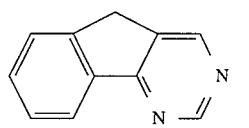 <1>

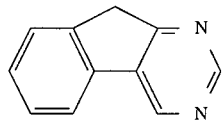 <1>

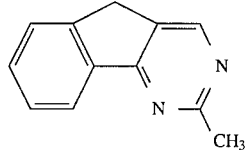 <2>

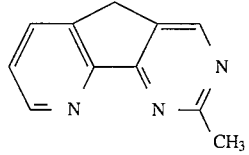 <3>

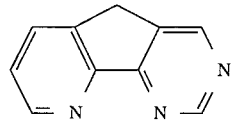 <3>

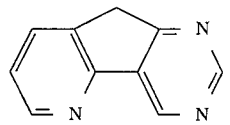 <3>

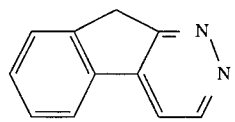 <4>

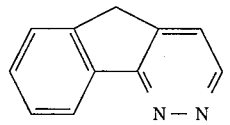 <5>

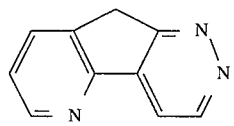 <6>

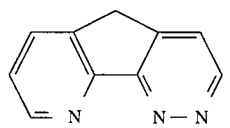 <6>

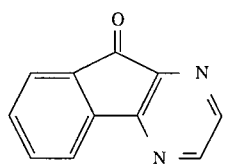 <7>

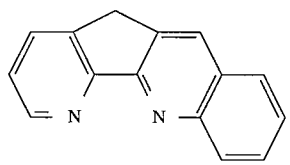 <8>

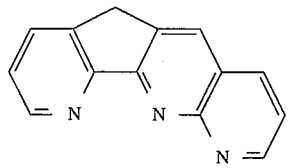 <8>

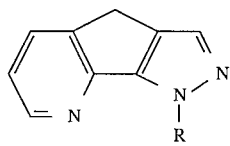 <9>

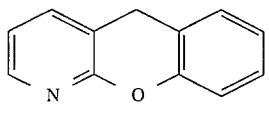 <10>

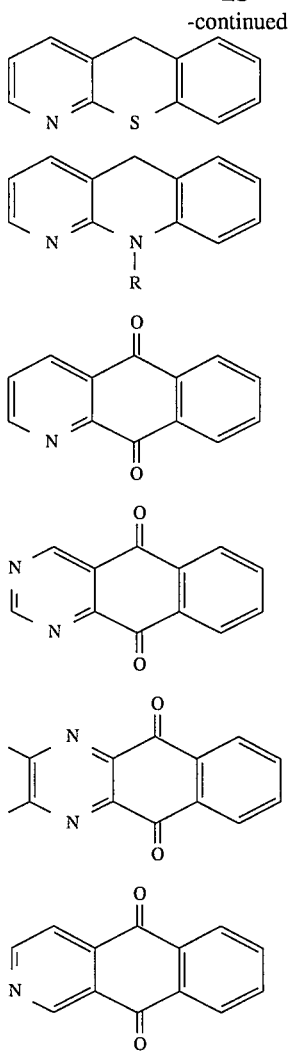

<1> *Chem Ber* 1971, 104, 2975–83;
<2> *J Med Chem* 1978, 21, 623–8;
<3> Prepared by analogy to <2>, using azaindanone rather than indanone. Other nitrogen positional isomers are also accessible.
<4> *Farmaco, Ed Sci* 1985, 40, 979–86;
<5> *Farmaco, Ed Sci* 1979, 34, 72–80;
<6> Prepared by analogy to <5>, using azaindanone rather than indanone. Other nitrogen positional isomers are also accessible.
<7> *Rend Accad Sci Fis Mat,* Naples 1983, 20, 353–6;
<8> *Tetrahedron* 1991, 47, 6851–6886
<9> Prepared by analogy to the above, using azaindanone rather than indanone. Other nitrogen positional isomers are also accessible; see *Heterocycles* 1991, 32, 41–72.
<10> *J Med Chem* 1975, 18, 1–8 and *Yakugaku Zasshi* 1976, 96, 99–109;
<11> Prepared by analogy to <10>;
<12> *J Org Chem* 1986, 51, 2011–21;
<13> *Heterocycles* 1988, 27, 2643–50;

<11> Reduction of anthraquinones to anthrones can be accomplished using sodium dithionate as described in *J Chem Soc* 1954, 274–8; *J. Org Chem* 1979, 44, 632–3; or by using lithium aluminum hydride as described in *J Org Chem* 1981, 46, 1552–7;.

Synthesis

Compounds of Formula I wherein R is —$CH_2$-(Het-2), and Het-1=Het-2, can be prepared from the appropriate "core group" as illustrated in Scheme I.

Scheme I

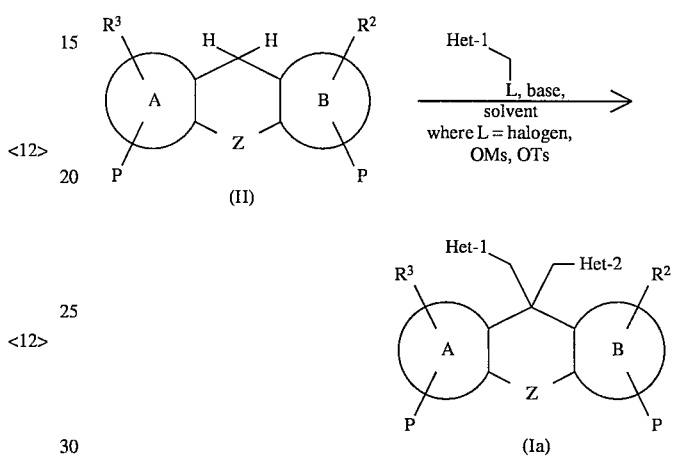

Suitable bases for forming the anion include, but are not limited to, sodium or potassium hydroxide, sodamide, lithium diisopropylamide (LDA), sodium hydride, potassium tert-butoxide, sodium alkoxide, potassium alkoxide, potassium hydride, lithium 2,2,6,6-tetramethylpiperidide, butyllithium, sec-butyl lithium, tert-butyl lithium, and lithium- sodium-, or potassium hexamethyldisilazide. The reaction can be conducted in an aprotic solvent, generally in an ether, such as but not limited to, tetrahydrofuran (THF), dioxane, glyme, diglyme, or diethyl ether ($Et_2O$); or benzene or toluene. Additionally, the reaction can be run in dimethylformamide (DMF) or dimethylacetamide (DMAC). However, if the reactants are soluble in a nonpolar solvent, the reaction can be carried out in a hydrocarbon solvent such as hexanes, heptane, cyclohexane, methylcyclohexane, benzene or toluene. If the reactants are compatible with water, the reactions can be conducted in solvent systems containing water and any of the other above mentioned organic solvents. Depending on the strength of the base, the reactions can be conducted at temperature from −78° C. to solvent reflux temperature. Typically, a compound such as (II) is bis-alkylated to give Ia, by reacting (II) under phase transfer conditions (PTC). The active methylene species (II) is suspended in a mixture of 50% sodium hydroxide and toluene containing a catalytic amount of PTC-catalyst such as tetrabutylammonium iodide or bromide, and treating the mixture dropwise with an aqueous solution of, for example, 4-picolyl chloride hydrochloride (2.2 equivalents) to give Ia.

Alternatively, compounds of Formula I, wherein R is other than —CH$_2$-(Het-2) or Het-1≠Het-2, can be synthesized by the sequence shown in Scheme II.

Scheme II

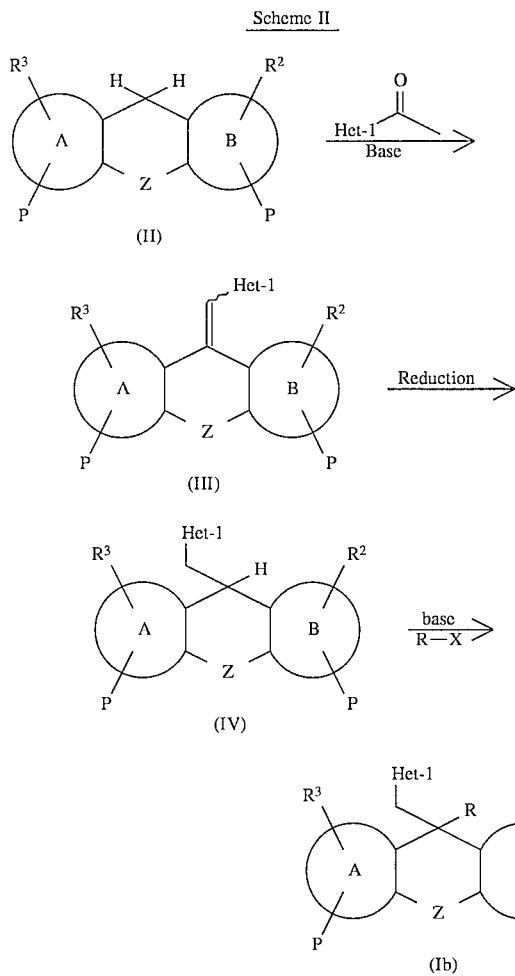

Methylene compound (II) is subjected to an aldol condensation with a suitably substitued pyridine or pyrimidine carboxaldehyde to give (III), which can be reduced with sodium borohydride, Pd/carbon and formic acid, Pd/carbon and hydrogen or dissolving metal conditions such as zinc in acetic acid to give (IV). Intermediate (IV) is dissolved in dry THF, cooled to 0° C., treated with 1.1 equivalents of sodium or potassium hexamethyldisilazide and a crown ether, stirred for 10 to 60 minutes under an inert gaseous environment, and treated dropwise with a dry THF solution of the alkylating agent X-R, where X is a leaving group, such as halogen, OSO$_2$Me or tosyl. The reaction mixture is stirred in the cold for one hour, and at ambient temperature until no starting material can be detected by chromatographic methods. The reaction mixture is concentrated at reduced pressure, and the residue is partitioned between water and methylene chloride. The organic phase is washed with water and brine, dried over anhydrous magnesium sulfate, filtered, and concentrated at reduced pressure. Depending on the purity, the compounds of this invention may be collected as an oil, gum, or amorphous solid; or recrystallized from an appropriate solvent system; or further purified by chromatographic, sublimation, or distillation processes. The compounds may also exist as the 'free base' or as an acid addition salt formed from pharmaceutically acceptable acids. Additionally, compounds of Formula (I) may exist as racemates, diastereomeric mixtures, or their optically pure isomers.

Alternatively, compounds of the present invention wherein X is other than hydrogen can be synthesized and incorporated into the compounds of the present invention using one of the intermediates described below. These compounds, when used in conjunction with methods previously described, along with methods known to one of skill in the art of organic synthesis, would allow for synthesis of compounds of Formula (I).

The substituted pyridine starting materials that are listed below are reported in the literature or are commercially available.

| $R^o$ | $R^m$ | $R^p$ | $R^{m'}$ | $R^{o'}$ | Ref. |
|---|---|---|---|---|---|
| Cl | CH$_2$Br | H | H | H | <1> |
| Cl | H | CH$_2$Br | H | H | <1> |
| Cl | H | H | CH$_2$Br | H | <1> |
| Cl | H | H | H | CH$_2$Br | <1> |
| Cl | CO$_2$Me | H | H | CH$_3$ | <2> |
| Cl | H | CO$_2$Me | H | CH$_3$ | <3> |
| Cl | H | H | CO$_2$Me | CH$_3$ | <4> |
| CH$_3$ | Cl | H | H | H | <5> |
| H | Cl | CH$_3$ | H | H | <6> |
| H | Cl | H | CH$_3$ | H | <7> |
| H | Cl | H | H | CH$_3$ | <8> |
| CH$_3$ | H | Cl | H | H | <9> |
| H | CH$_3$ | Cl | H | H | <10> |
| CH$_2$OH | H | Cl | H | H | <11> |
| F | CN | H | H | CH3 | <12> |
| F | CH$_2$Br | H | H | H | <13> |
| F | H | CH$_2$Br | H | H | <13> |
| F | H | H | CH$_2$Br | H | <13> |
| F | H | H | H | CH$_2$Br | <13> |
| CH$_2$OH | F | H | H | H | <8> |
| H | F | CH$_3$ | H | H | <14> |
| H | F | H | CH$_2$OH | H | <15> |
| H | F | H | CH$_3$ | H | <15> |
| H | F | H | COOH | H | <16> |
| H | F | H | H | CH$_2$OH | <8> |
| CH$_3$ | H | F | H | H | <17> |
| H | CH$_3$ | F | H | H | <17> |
| Br | H | CH$_2$Br | H | H | <1> |
| Br | H | H | CH$_2$Br | H | <1> |
| Br | H | H | H | CH$_2$Br | <1> |
| CH$_3$ | Br | H | H | H | <18> |
| H | Br | CH$_3$ | H | H | <19> |
| H | Br | H | CO$_2$Et | H | commercial |
| H | Br | H | H | CH$_3$ | <8> |
| CH$_3$ | H | Br | H | H | <20> |
| H | CH$_3$ | Br | H | H | <21> |
| NH$_2$ | CO$_2$Me | H | H | CH$_3$ | <22> |
| H | NH$_2$ | H | CH$_3$ | H | <15> |
| NH$_2$ | CH$_3$ | H | H | H | commercial |
| NH$_2$ | H | CH$_3$ | H | H | commercial |
| NH$_2$ | H | H | CH$_3$ | H | commercial |
| NH$_2$ | H | H | H | CH$_3$ | commercial |
| NO$_2$ | H | H | H | CH$_2$OH | <20> |
| NO$_2$ | CO$_2$Me | H | H | CH$_3$ | <23> |
| NO$_2$ | H | COOH | H | CH$_3$ | <23> |
| NO$_2$ | H | H | CO$_2$Me | CH$_3$ | <23> |
| NO$_2$ | CH$_2$Br | H | H | H | <24> |
| NO$_2$ | H | H | H | CH$_2$Br | <25> |
| CH$_3$ | NO$_2$ | H | H | H | <26> |

-continued

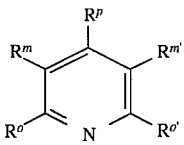

| R$^o$ | R$^m$ | R$^p$ | R$^{m'}$ | R$^{o'}$ | Ref. |
|---|---|---|---|---|---|
| H | NO$_2$ | CH$_3$ | H | H | <27> |
| H | NO$_2$ | H | CH$_3$ | H | <28> |
| H | NO$_2$ | H | H | CH$_3$ | <29> |
| CH$_3$ | H | NO$_2$ | H | H | <20> |
| H | CH$_3$ | NO$_2$ | H | H | commercial |
| NO$_2$ | H | CH$_3$ | H | H | <30> |
| NO$_2$ | H | H | CH$_3$ | H | <30> |
| CF$_3$ | CH$_2$OH | H | H | H | <20> |
| CF$_3$ | H | CH$_2$OH | H | H | <20> |
| CF$_3$ | H | H | H | CH$_2$OH | <20> |
| CF$_3$ | H | CO$_2$Et | H | CH$_3$ | <31> |
| CF$_3$ | H | H | CH$_2$Br | H | <32> |
| CH$_3$ | CF$_3$ | H | H | H | <20> |
| H | CF$_3$ | H | CH$_3$ | H | <20> |
| H | CF$_3$ | H | H | CH$_2$OH | <8> |
| CH$_3$ | H | CF$_3$ | H | H | <20> |
| CN | H | CH$_2$Cl | H | H | <33> |
| CN | H | H | CH$_2$Cl | H | <34> |
| CN | H | H | H | CH$_2$Cl | <35> |
| CN | CO$_2$Me | H | H | CH$_3$ | <36> |
| CN | H | H | CH$_2$OCH$_3$ | CH$_3$ | <37> |
| CN | CH$_2$Br | H | H | H | <38> |
| CN | H | H | CO$_2$Me | CH$_3$ | <39> |
| CH$_2$Br | CN | H | H | H | <38> |
| H | CN | CH$_2$Br | H | H | <38> |
| H | CN | H | CH$_3$ | H | <40> |
| H | CN | H | H | CH$_3$ | <41> |
| CH$_2$OH | H | CN | H | H | <11> |
| H | CH$_2$Br | CN | H | H | <38> |
| CH$_3$ | CH$_2$Cl | H | H | H | <42> |
| CH$_3$ | H | CH$_2$Cl | H | H | <43> |
| CH$_3$ | H | H | CH$_2$Cl | H | <42> |
| CH$_3$ | CO$_2$Me | H | H | CH$_3$ | <3> |
| CH$_3$ | H | CH$_2$Cl | H | CH$_3$ | <44> |
| CH$_3$ | H | CH$_2$Br | H | H | <11> |
| CH$_3$ | H | H | H | CH$_2$Br | <45> |
| CH$_3$ | H | CH$_2$OH | H | CH$_3$ | <11> |
| CH$_3$ | CH$_2$OH | H | H | H | <46> |
| CH$_3$ | H | H | H | CH$_2$OH | <11> |
| CH$_2$OH | CH$_3$ | H | H | H | <8> |
| CH$_2$OH | H | CH$_3$ | H | H | <8> |
| CH$_2$OH | H | H | CH$_3$ | H | <8> |
| H | CH$_3$ | CO$_2$Me | H | H | <38> |
| H | CH$_2$Br | CH$_3$ | H | H | <42> |
| H | CH$_2$Br | H | CH$_3$ | H | <42> |
| H | CH$_2$OH | H | CH$_3$ | H | <15> |
| I | H | CO$_2$Me | H | CH$_3$ | <47> |
| H | I | H | H | CH$_2$OH | <8> |

<1> J. Med. Chem. 1971 14 557–8
<2> U.S. Pat. No. 4,215,123
<3> J. Am. Chem. Soc. 1959 81 704–9
<4> Germa Patent No. DE 2020762
<5> Pol. J. Chem. 1991 65 289–95
<6> J. Organomet. Chem. 1981 216 139–47
<7> Europ. Pat. Application No. 284174
<8> J. Med. Chem. 1970 13 1124–30
<9> U.S. Pat. No. 3,467,659
<10> J. Heterocycl. Chem. 1988 25 81–7
<11> Synth. Commun. 1989 19 317–25
<12> Acta Pol. Pharm. 1974 31 439
<13> J. Med. Chem. 1971 14 211–4
<14> Acta Crystallogr., Sect. C: Cryst. Struct. Commun. 1985 C41 785–8
<15> J. Org. Chem. 1988 53 3513–21
<16> J. Org. Chem. 1949 14 328
<17> Rocz. Chem. 1970 44 1249–53
<18> J. Med. Chem. 1987 30 871–80
<19> J. Heterocycl. Chem. 1973 10 711–14
<20> Chem. Pharm. Bull. 1990–38 2446–58
<21> Heterocycles 1992 34 1605–12
<22> J. Med. Chem. 1987 30 2270–7
<23> J. Med. Chem. 1978 21 194–9
<24> J. Chem. Soc. C 1967 1564–8
<25> Farmaco, Ed. Sci. 1982 37 398–410
<26> J. Heterocycl. Chem. 1992 29 359–67
<27> J. Org. Chem. 1957 22 138–40
<28> Bull. Chem. Soc. Jpn. 1990 63 2820–7
<29> Synth. Commun. 1990 20 2965–70
<30> J. Am. Chem. Soc. 1951 73 494
<31> J. Med. Chem. 1973 16 68–72
<32> Europ. Pat. Application No. 212600
<33> U.S. Pat. No. 4,156,734
<34> Europ. Pat. Application No. 539086
<35> Europ. Pat. Application No. 417751
<36> Aust. J. Chem. 1982 35 1451–68
<37> J. Chem. Soc., Perkin Trans. 1 1975 2102–4
<38> J. Prakt. Chem. 1987 329 557–62
<39> Japanese Patent No. 03181464
<40> Europ. Pat. Application No. 2533660
<41> Europ. Pat. Application No. 104876
<42> J. Med. Chem. 1991 34 1028–36
<43> Farmaco, Ed. Sci. 1980 35 621–35
<44> Europ. Pat. Application No. 302389
<45> J. Chem. Soc. 1958 3594–3603
<46> J. Org. Chem. 1981 46 2059–65
<47> Cesk. Farm. 1969 18 341–5

The preparation of substituted methylpyridines is outlined in Scheme III.

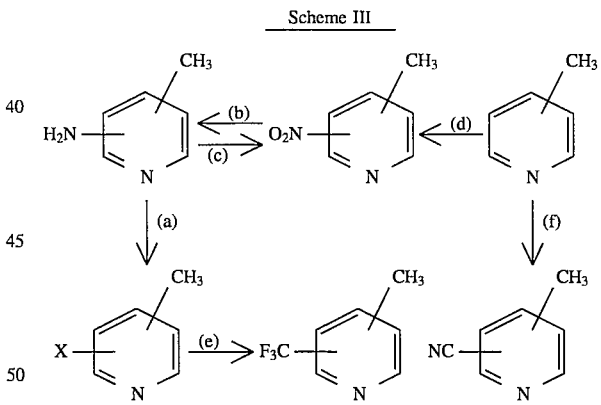

Scheme III

Reagents:
(a) NANO$_2$, HX, CuX$_2$;
(b) H$_2$, Pd/C or SnCl$_2$;
(c) H$_2$O$_2$, H$_2$SO$_4$;
(d) HNO$_3$, H$_2$SO$_4$;
(e) CF$_3$I, Cu, HMPT;
(f) 1) MCPBA, 2) KCN.

Additionally, where preparation of substituted and unsubstituted halo-methylene pyridines of the present invention are not described in the literature, conversions from known starting materials and intermediates is outlined in Scheme IV.

Scheme IV

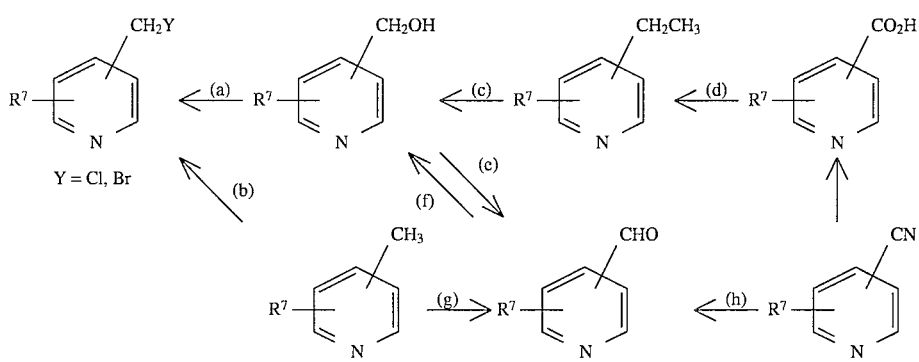

Reagents:
(a) CBr$_4$, PPh$_3$;
(b) NCS or NBS;
(c) NaBH$_4$, MeOH;
(d) 1) SOCl$_2$, 2) MeOH;
(e) PCC;
(f) NaBH$_4$;
(g) I$_2$/DMSO;
(h) DIBAL-H.

Compounds of Formula I wherein Het-1 or Het-2 are substituted pyrimidines are prepared from substituted pyrimidine starting materials which are either commercially available or reported in the literature, such as those listed below.

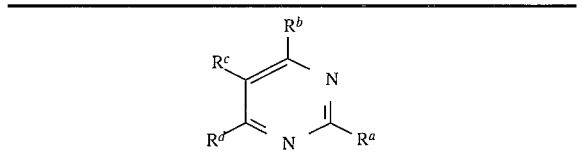

| $R^a$ | $R^b$ | $R^c$ | $R^d$ | Ref. |
|---|---|---|---|---|
| F | CH$_3$ | H | H | <1> |
| F | H | CH$_3$ | H | <2> |
| Cl | CH$_3$ | H | H | commercial |
| Cl | H | CH$_3$ | H | <3> |
| Br | CH$_3$ | H | H | <4> |
| Br | H | CH$_3$ | H | <5> |
| NH$_2$ | CH$_3$ | H | H | commercial |
| NH$_2$ | H | CH$_3$ | H | <6> |
| CN | CH$_3$ | H | H | <7> |
| CN | H | CH$_3$ | H | <8> |
| CH$_3$ | F | H | H | <1> |
| H | F | H | CH$_3$ | <1> |
| CH$_3$ | Cl | H | H | <9> |
| H | Cl | CH$_3$ | H | <10> |
| H | Cl | H | CH$_3$ | <11> |
| H | Br | H | CH$_3$ | <12> |
| CH$_3$ | NH$_2$ | H | H | <13> |
| H | NH$_2$ | CH$_3$ | H | <14> |
| H | NH$_2$ | H | CH$_3$ | <15> |
| CH$_3$ | CF$_3$ | H | H | <16> |
| CH$_3$ | CN | H | H | <7> |
| H | CN | CH$_3$ | H | <17> |
| H | CN | H | CH$_3$ | <18> |
| CH$_3$ | H | F | H | <19> |
| CH$_3$ | H | Cl | H | <20> |
| H | CH$_3$ | Cl | H | <17> |
| CH$_3$ | H | Br | H | <21> |
| H | CH$_3$ | Br | H | <17> |
| CH$_3$ | H | NH$_2$ | H | <22> |

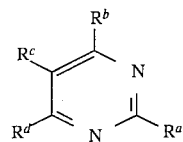

| $R^a$ | $R^b$ | $R^c$ | $R^d$ | Ref. |
|---|---|---|---|---|
| H | CH$_3$ | NH$_2$ | H | <15> |
| CH$_3$ | H | NO$_2$ | H | <23> |
| H | CH$_3$ | NO$_2$ | H | <24> |
| CH$_3$ | H | CN | H | <25> |

<1> *J. Chem. Soc., Perkin Trans.* 2 1974 204–8
<2> *Izv. Sib. Otd. Akad. Nauk SSSR, Ser. Khim. Nauk* 1977 106–9
<3> *Aust. J. Chem.* 1977 30 2515–25
<4> *Helv. Chim. Acta* 1992 75 1621–32
<5> Japanese Patent No. 05085972
<6> *J. Am. Chem. Soc.* 1990 112 7736–42
<7> *Synthesis* 1984 681–3
<8> *Collect. Czech. Chem. Commun.* 1972 37 1721–33
<9> German Patent No. 3905364
<10> *J. Org. Chem.* 1984 49 296–300
<11> *Chem. Ber.* 1899 32 2921
<12> *Recl. Trav. Chim. Pays-Bas* 1979 98 5–8
<13> *J. Heterocycl. Chem.* 1977 14 1413–14
<14> *J. Org. Chem.* 1970 35 438–41
<15> *J. Chem. Soc.* 1951 1004
<16> *Farmaco* 1993 48 335–55
<17> *Chem. Pharm. Bull.* 1987 35 3119–26
<18> *Liebigs Ann. Chem.* 1981 333–41
<19> *Justus Liebigs Ann. Chem.* 1975 470–83
<20> *Aust. J. Chem.* 1974 27 2251–9
<21> *Collect. Czech. Chem. Commun.* 1949 14 223
<22> *J. Org. Chem.* 1964 29 941
<23> *J. Org. Chem.* 1982 47 1077–80
<24> *J. Org. Chem.* 1986 51 67–71
<25> *J. Chem. Soc. C* 1966 649

Additional compounds of Formula I can be prepared via functional group conversions of compounds within the scope of this invention using standard methodology known to one of skill in the art of organic synthesis. Several examples of such conversions are shown in Scheme V.

Scheme V

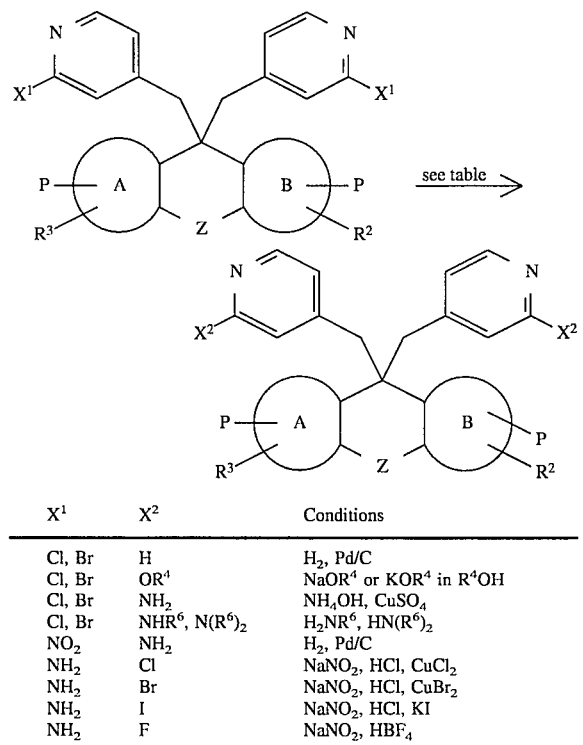

| $X^1$ | $X^2$ | Conditions |
| --- | --- | --- |
| Cl, Br | H | $H_2$, Pd/C |
| Cl, Br | $OR^4$ | $NaOR^4$ or $KOR^4$ in $R^4OH$ |
| Cl, Br | $NH_2$ | $NH_4OH$, $CuSO_4$ |
| Cl, Br | $NHR^6$, $N(R^6)_2$ | $H_2NR^6$, $HN(R^6)_2$ |
| $NO_2$ | $NH_2$ | $H_2$, Pd/C |
| $NH_2$ | Cl | $NaNO_2$, HCl, $CuCl_2$ |
| $NH_2$ | Br | $NaNO_2$, HCl, $CuBr_2$ |
| $NH_2$ | I | $NaNO_2$, HCl, KI |
| $NH_2$ | F | $NaNO_2$, $HBF_4$ |

Other representative compounds of this invention can be synthesized in an analogous fashion by using methods commonly known to one skilled in the art of organic synthesis, i.e., by converting a $R^2$, $R^3$ or Y-group to another functional group. One such example, as in the case of an ester ($CO_2R^5$) being converted to the corresponding acid ($CO_2H$); or alcohol (OH) which can be further converted to an ether ($OR^5$) or the 'reverse ester' (O—$COR^5$). For such a case, the ester can be saponified to give the acid ($CO_2H$) which can be reduced to the alcohol. Alternatively, the ester can be directly reduced to the alcohol. An alternative approach to the 'reverse ester' compounds (—OC(=O)$R^5$), can be initiated with the ester, which can be reduced to the alcohol, which can be subsequently acylated with an acid halide or anhydride, or by coupling the alcohol to an acid using N,N-dicyclohexyl-carbodiimide, carbonyl diimidazole, or some other coupling agent known to one of skill in the art.

A nitrile can be hydrated to the corresponding amide using the procedure described by Noller, *Org. Syn, Coll.* Vol. II: p 586. The same amide can be prepared from the corresponding ester by saponification, activation of carboxyl, and reaction with ammonia. By substituting primary or secondary amines for ammonia, other amides of this invention may be prepared. The corresponding amines can be obtained by reduction of the amides.

The compounds of the invention and their synthesis are further illustrated by the following examples and preparations. All temperatures are in degrees Celsius.

Preparation 1

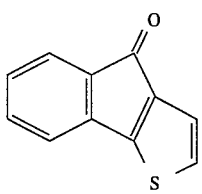

A 500 ml three-neck round bottom flask was charged with zinc chloride (75 ml, 1.0M in $Et_2O$) and cooled to 0° C. A solution of 2-thienyllithium (75 ml, 1.0M in THF) was added via dropping funnel over a 30 min period. The biphasic solution was stirred for an additional hour, then transferred via cannula to a solution of methyl 2-iodobenzoate (13.1 g, 0.05 mole), tetrakis(triphenylphosphine) palladium (2.9 g, 0.0025 mole) in THF (120 ml). The reaction was allowed to stir at room temperature overnight. Water (500 ml) was added, and the resulting emulsion was filter through Celite. The organic phase was separated, and the aqueous was extracted with EtOAc (1×500 ml, 2×250 ml). The combined EtOAc extract was washed with brine, dried over $Na_2SO_4$, filtered, then further dried over $MgSO_4$. Following filtration and concentration, the crude ester was directly saponified with KOH (5.61 g, 0.10 mole), water (16.5 ml) and EtOH (65 ml) at reflux for one hour. The reaction was concentrated at 30° C., diluted with water (200 ml), washed with EtOAc (3×50 ml), $Et_2O$ (1×50 ml) and filtered through Celite. The aqueous was acidified with conc. HCl and extracted with EtOAc (3×100 ml). The organic layer was washed with brine, dried over $MgSO_4$, filtered, concentrated and azeotroped with benzene. The resulting brown oil was refrigerated overnight to render the acid (10.0 g) in quantitative yield.

The impure acid was dissolved in benzene (113 ml) and treated at room temperature with oxalyl chloride (4.7 ml, 0.053 mole) and cat DMF. Following stirring for 1 hour the reaction was evaporated in vacuo. The residue was redissolved in benzene (113 ml) at 4° C. and tin (IV) chloride (5.7 ml, 0.053 mole) was added. The reaction was stirred for 15 min (or until complete as judged by TLC), quenched with water and 1N HCl until homogeneous and extracted with $Et_2O$. The $Et_2O$ extract was worked up in the usual manner and the crude product was purified on silica gel using 5/1 hexane/ether to give the title compound (5.8 g) in 58% yield; mp 99°–100° C. Variations of this procedure include the use of 2-thiophene trimethyltin instead of 2-thienyllithium, and the use of thionyl chloride instead of oxalyl chloride to form the acid chloride.

Preparation 2

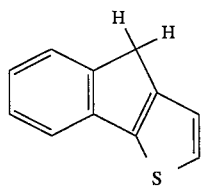

A solution of starting ketone in Preparation 1 (1.28 g) was allowed to heat in diethylene glycol at 160° C. before addition of hydrazine (13.9 ml) and elevation of temperature to 200° C. for 40 min. Upon cooling and dilution with water, Preparation of 2-Fluoro-4-chloromethylpyridine To a 1000 ml Single Neck RBF, equipped with a magnetic stirrer, reflux condenser, heating mantle was added 2-fluoro-4-picoline (13.33 g, 120 mmol) and carbon tetrachloride (~250 ml), N-chlorosuccinimide (23.98 g, 180 mmol, 1.5 eq.) and benzoyl peroxide (1.5 g). The reaction was heated to reflux for 6 hours, additional benzoyl peroxide (1.5 g) was added and the heating maintained overnight. Monitor by TLC (1:1 toluene/methylene chloride). [At higher concentrations, more di-chloro product is formed.] The reaction was worked up by cooling to room temperature or below, filtered through Celite, and the precipatate was washed with more $CCl_4$. The organic solution was washed with sat. sodium thiosulfate ($Na_2S_2O_3$), saturated sodium bicarbonate, water, and brine. Following drying over magnesium sulfate, the filtrate was evaporated to an oil, determine product ratio by NMR. This material can be used in the next step without further purification. [For the two batches of the above reaction was obtained 32.94 g product mixture, which was 60% desired product, 16% di-chloro, and 24% SM.]

EXAMPLE 1

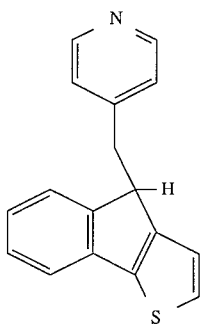

4-(4-Pyridinylmethyl)-4H-indeno[1,2-B]thiophene

A solution of methylene compound from Preparation 2 (1.87 g, 0.011 mole) was reacted with 4-pyridine carboxaldehyde (1.05 ml, 0.011 mole), KO$^t$Bu (1.35 g, 0.012 mole) in THF (40 ml) for 5 min. The reaction was quenched with saturated $NH_4Cl$ (100 ml) and extracted with $CH_2Cl_2$ (3×50 ml). The combined $CH_2Cl_2$ extract was washed with additional $NH_4Cl$, dried over $MgSO_4$. Upon concentration in vacuo, the crude red oil was reacted with zinc (11.0 g) in AcOH (50 ml) at reflux. Normal neutralization and extractive work up gave the title compound as a solid in 75% yield; mp 91°–93° C. (hexane/ethyl acetate).

Preparation 3

General alkylation method

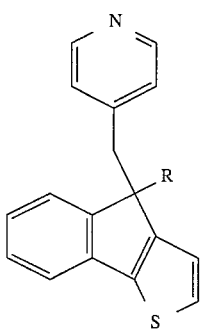

To a solution of Example 1 (1 equiv.) and 18-crown-6 (0.1 equiv.) in THF (50 ml per 2 mmol) was added at 0° C. potassium hexamethyldisilazide (1 equiv.), followed by stirring for 45 min. The electrophile (R—Br) [always a bromide] (1 equiv.) in THF (10 ml) was added and the reaction was stirred at room temperature overnight. The reaction was quenched in $CHCl_3$/satd. $NH_4Cl$ (50 ml each). Following further extraction with $CHCl_3$, the combined $CHCl_3$ extract was washed with brine, dried over $MgSO_4$, filtered and concentrated. The crude residue was purified by column chromatography on silica gel using MeOH/$CHCl_3$ to give the free base. Characterization was typically done by way of the mineral acid salt (HCl or HBr); however, in some instances, the free base was preferred.

EXAMPLE 2

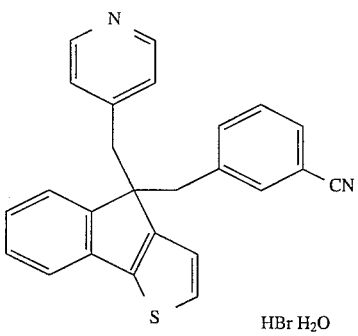

3-[4-(4-Pyridinylmethyl)-4H-indeno[1,2-B] thiophen-4-ylmethyl-benzonitrile Hydrobromide Hydrate By using 3-cyanobenzyl bromide in Procedure 3, the title compound ($C_{25}H_{18}N_2S$ HBr $H_2O$) was obtained in 92% yield; mp 246–251 dec.

EXAMPLE 3

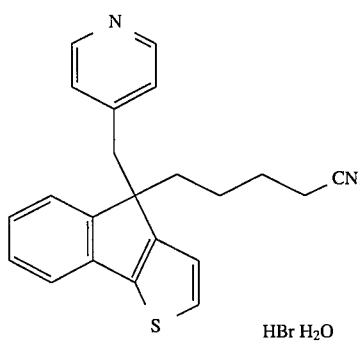

4-(4-Pyridinylmethyl)-4H-indeno[1,2-B]
thiophene-4-pentanenitrile Hydrobromide Hydrate By using 5-bromo valeronitrile in Procedure 3, the title compound ($C_{22}H_{20}N_2S$ HBr $H_2O$) was obtained in 33% yield; mp 136° C. (dec).

EXAMPLE 4

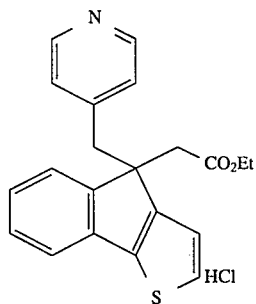

4-(4-Pyridinylmethyl)-4H-indeno[1,2-B]
thiophene-4-acetic acid, Ethyl Ester Hydrochloride By using ethyl 2-bromoacetate in Procedure 3, the title compound ($C_{21}H_{19}N_2OS$ HCl) was obtained in 75% yield; mp 183°–187° C.

EXAMPLE 5

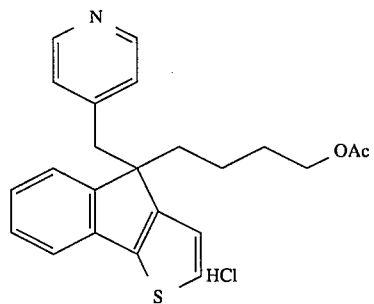

4-(4-Pyridinylmethyl)-4H-indeno[1,2-B]
thiophene-4-butanol Acetate (Ester) Hydrochloride By using 4-bromobutyl acetate in Procedure 3, the title compound ($C_{23}H_{23}NO_2S$ HCl) was obtained in 69% yield; mp 186°–190° C. Example 6

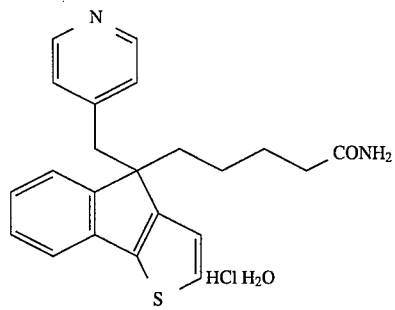

4-(4-Pyridinylmethyl)-4H-indeno[1,2-B]
thiophene-4-pentanamide Hydrochloride Hydrate Using the method described by Noller, *Org. Syn. Coll.* Vol. II, p 586, the nitrile in Example 3 was converted to the corresponding amide, ($C_{22}H_{22}N_2OS$ HCl $H_2O$) in 65% yield; mp 187°–190° C.

EXAMPLE 7

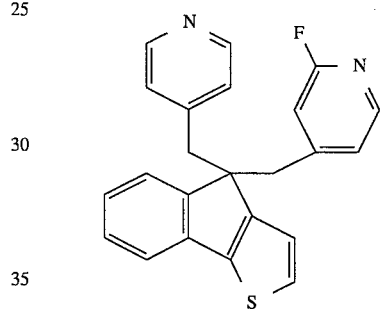

2-Fluoro-4-[4-(4-pyridinylmethyl)-4H-indeno[1,2-B]
thiophen-4-ylmethyl]-pyridine By using 2-fluoro-4-picolyl chloride in Procedure 3, the title compound ($C_{23}H_{17}FN_2S$) was obtained in 57% yield; mp 117°–119° C.

EXAMPLE 8

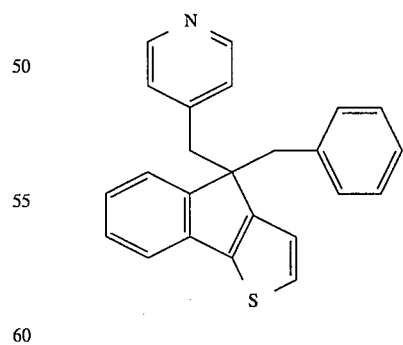

4-[4-(Phenyl)-4H-indeno[1,2-B]
thiophen-4-ylmethyl]-pyridine

By using benzyl bromide in Procedure 3, the title compound ($C_{24}H_{19}NS$) was obtained in 20% yield; mp 88°–92° C.

EXAMPLE 9

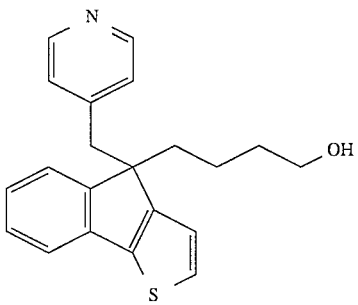

4-(4-Pyridinylmethyl)-4H-indeno[1,2-B]
thiophene-4-butanol

By subjecting the product of Example 5 to alkaline hydrolysis, the title compound was isolated as an oil in quantitative yield; $C_{21}H_{21}NOS$, MW 335.45, mass spec 336(M+1).

Preparation 4

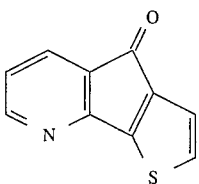

By a procedure analogous to that described in Preparation 1, and substituting methyl-2-bromo-nicotinate, the title compound can be prepared.

EXAMPLE 10

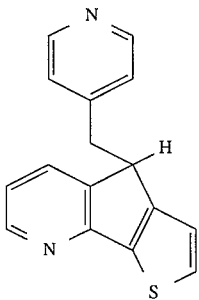

4-(4-Pyridinylmethyl)-4H-thieno[2',3':3,4]
cyclopenta[1,2-B]pyridine

By substituting the product from Procedure 4 into Procedures 2 and 3, the title compound ($C_{16}H_{12}N_2S$) was obtained in 45% yield; mp 178°–181° C.

EXAMPLE 11

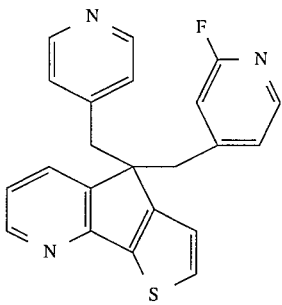

4-[(2-Fluoro-4-pyridinyl)methyl]-4-
(4-pyridinylmethyl)-4H-thieno
[3',2':4,5]cyclopenta[1,2-B]pyridine By substituting Example 10 as starting material in Procedure 3 and using 2-fluoro-4-picolyl choride, the title compound ($C_{22}H_{16}FN_3S$) was obtained in 92% yield; mp 192°–193° C.

EXAMPLE 12

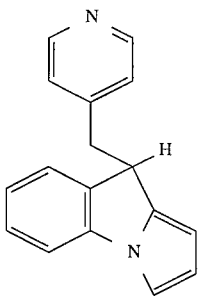

Using 9H-Pyrrolo[1,2a]indole, which was prepared by the method described by Mazzola, V. J., et al.; *J. Org. Chem.*, (1967) 32: 486, in the procedure described for Example 1, the desired mono-picolyl product could be obtained.

EXAMPLE 13

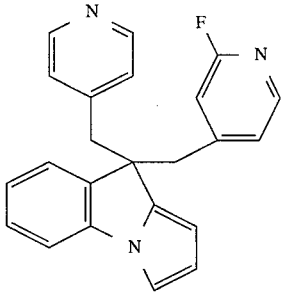

9-(4-pyridinylmethyl)9-((2-fluoro-4-pyridinyl)
methyl)-9H-pyrrolo[1,2-A]indole

By substituting Example 12 as starting material for the preparation of Example 11, the title compound could be obtained.

EXAMPLE 14

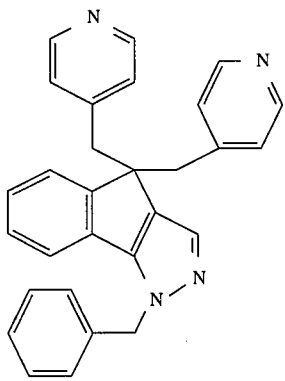

1,4-Dihydro-1-(phenylmethyl)-4,4-bis (4-pyridinylmethyl)indeno[1,2-C]pyrazole A solution of N-benzyl pyrazzoindene (6.1 mmol) in 10 ml DMSO was added dropwise to a mixture of KO'Bu (1.44 g, 12.8 mmol) in 20 ml DMSO/Et$_2$O (1:1) at 10° C. while stirring under dry nitrogen. The mixture was treated dropwise over 30 min with a solution of 4-picolyl chloride (free base) (14.6 mmol) in 30 ml Et$_2$O. The mixture was stirred at room temperature for 16 hr and poured into 100 ml water. The mixture was extracted with 100 ml Et$_2$O. The extract was washed with water and brine, dried over MgSO$_4$, filtered, and concentrated in vacuo to a foam (1.8 g). The foam was column chromatographed on silica gel using CH$_2$Cl$_2$ as mobile phase. Appropriate fractions were combined and concentrated in vacuo. The residue was recrystallized from EtOAc/hexanes to give the title compound in 74% yield; mp 154°–155° C.; Anal calcd for C$_{29}$H$_{24}$N$_4$: C, 81.28; H, 5.65; N, 13.08. Found: C, 80.73; H, 5.77; N, 12.82. Mass spec m/e 429(M+1).

EXAMPLE 15

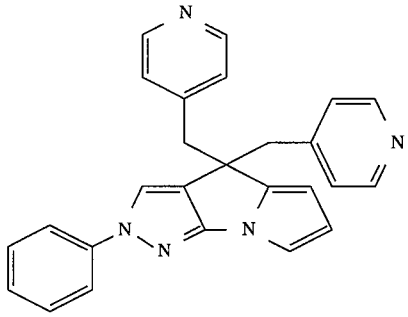

2,4-Dihydro-2-phenyl-4,4-bis(4-pyridinylmethyl) pyrazolo[4,3-B]pyrrolizine

To a solution of 2,4-dihydro-2-phenylpyrazolo[4,3-B]pyrrolizine (6.1 mmol) and 18-Crown-6 (6.1 mmol) in tetrahydrofuran at 0° C. was added potassium hexamethyldisilazide, followed by 4-picolyl chloride (14.6 mmol, freebased in toluene) and the reaction allowed to warm to room temperature overnight. Following normal extractive workup and purification, the title compound was isolated as a solid in 4% yield; mp 169°–170° C.; Anal calc'd. for C$_{26}$H$_{21}$N$_5$: C, 77.40; H, 5.25; N, 17.36. Found: C, 77.01; H, 5.12; N, 17.18. Mass spec m/e 404 (M+1).

By using the methods illustrated in the above examples, the compounds in Table I were prepared.

TABLE I ($R^2 = R^3 = H$)

| Ex | A | B | R | m.p. °C. |
|----|-----|---------|-------------------------|----------|
| 1  | (Phe) | (2,3-Thi) | H | 91–93 |
| 2  | Phe | 2,3-Thi | —CH$_2$-3-CN—C$_6$H$_5$ | 246–251 |
| 3  | Phe | 2,3-Thi | —(CH$_2$)$_4$CN | 136 |
| 4  | Phe | 2,3-Thi | —CH$_2$—CO$_2$Et | 183–187 |
| 5  | Phe | 2,3-Thi | —(CH$_2$)$_4$—OAc | 186–190 |
| 6  | Phe | 2,3-Thi | —(CH$_2$)$_4$—CONH$_2$ | 187–190 |
| 7  | Phe | 2,3-Thi | —CH$_2$-2-F—(4-Pyr) | 117–119 |
| 8  | Phe | 2,3-Thi | —CH$_2$—C$_6$H$_5$ | 88–92 |
| 9  | Phe | 2,3-Thi | —(CH$_2$)$_4$—OH | oil |

TABLE I-continued

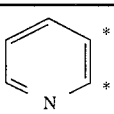

(R² = R³ = H)

| Ex | A | B | R | m.p. °C. |
|---|---|---|---|---|
| 10 | 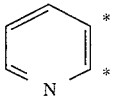<br>(2,3-Pyr) | 2,3-Thi | H | 178–181 |
| 11 | 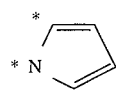<br>(2,3-Pyr) | 2,3-Thi | —CH₂-2-F-4-Pyr | 192–193 |
| 12 | Phe | 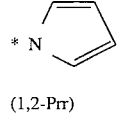<br>(1,2-Prr) | H | |
| 13 | Phe | 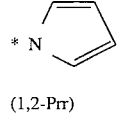<br>(1,2-Prr) | —CH₂-2-F-4-Pyr | |
| 14 | Phe | 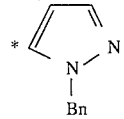<br>(N—Bn-4,5-Pyz) | —CH₂-4-Pyr | 154–155 |
| 15 | 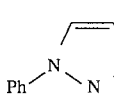 | 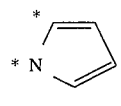<br>(1,2-Prr) | —CH₂-4-Pyr | 169–170 |
| 16 | Phe | N—Ph-4,5-Pyz | —CH₂-4-Pyr | |
| 17 | Phe | N—Ph-4,5-Pyz | —CH₂-2-F-4-Pyr | |
| 18 | Phe | 2,3-Thi | —(CH₂)₂—CO₂Et | |
| 19 | Phe | 2,3-Thi | —(CH₂)₃—CO₂Et | |
| 20 | Phe | 2,3-Thi | —(CH₂)₄—CO₂Et | |
| 21 | Phe | 2,3-Thi | —(CH₂)₅—CO₂Et | |
| 22 | Phe | 2,3-Thi | —(CH₂)₂—CN | |
| 23 | Phe | 2,3-Thi | —(CH₂)₃—CN | |
| 24 | Phe | 2,3-Thi | —(CH₂)₆—CN | |
| 25 | Phe | 2,3-Thi | —(CH₂)₂—OCOCH₃ | |
| 26 | Phe | 2,3-Thi | —(CH₂)₃—OCOCH₃ | |
| 27 | Phe | 2,3-Thi | —(CH₂)₄—OCOCH₃ | |
| 28 | Phe | 2,3-Thi | —(CH₂)₅—OCOCH₃ | |

TABLE I-continued

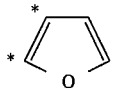

(R² = R³ = H)

| Ex | A | B | R | m.p. °C. |
|---|---|---|---|---|
| 29 | Phe | 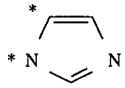 (2,3-Fur) | H | |
| 30 | Phe | 2,3-Fur | —CH₂-3-CN—C₆H₅ | |
| 31 | Phe | 2,3-Fur | —(CH₂)₄CN | |
| 32 | Phe | 2,3-Fur | —CH₂—CO₂Et | |
| 33 | Phe | 2,3-Fur | —(CH₂)₄—OAc | |
| 34 | Phe | 2,3-Fur | —(CH₂)₄—CONH₂ | |
| 35 | Phe | 2,3-Fur | —CH₂-2-F-(4-Pyr) | |
| 36 | Phe | 2,3-Fur | —CH₂—C₆H₅ | |
| 37 | Phe | 2,3-Fur | —(CH₂)₄—OH | |
| 38 | Phe | 2,3-Fur | —CH₂CH=CH—CO₂Et | |
| 39 | Phe | 2,3-Fur | 2-F-(4-Pyr)-CH₂ | |
| 40 | Phe | 2,3-Fur | —CH₂CH≡CH—CO₂Et | |
| 41 | Phe | 2,3-Fur | —CH₂-2-F-4-Pyr | |
| 42 | Phe | 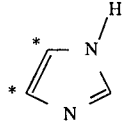 (1,5-Imi) | H | |
| 43 | Phe | 1,5-Imi | —CH₂-3-CN—C₆H₅ | |
| 44 | Phe | 1,5-Imi | —(CH₂)₄CN | |
| 45 | Phe | 1,5-Imi | —CH₂—CO₂Et | |
| 46 | Phe | 1,5-Imi | —(CH₂)₄—OAc | |
| 47 | Phe | (4,5-Imi) | —(CH₂)₄—CONH₂ | |
| 48 | Phe | 4,5-Imi | —CH₂-2-F-(4-Pyr) | |
| 49 | Phe | 4,5-Imi | —CH₂—C₆H₅ | |
| 50 | Phe | 4,5-Imi | —(CH₂)₄—OH | |
| 51 | Phe | 4,5-Imi | —CH₂CH=CH—CO₂Et | |
| 57 | 1,2-Pyr | 4,5-Imi | —CH₂-2-F-4-Pyr | |
| 58 | 1,2-Pyr | N—Bn-4,5-Pyz | —CH₂-2-F-4-Pyr | |
| 59 | 5,6-Pyr | N—Bn-4,5-Pyz | —CH₂-2-F-4-Pyr | |
| 60 | 1,2-Pyr | 1-Bn-2,3-Prr | —CH₂-2-F-4-Pyr | |

By using the methods illustrated in the above examples, the following compounds were also prepared.

EXAMPLE 61

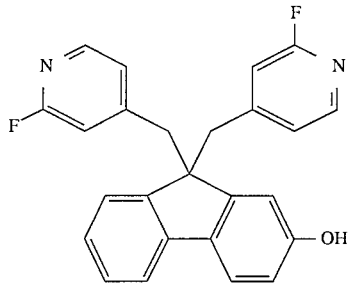

9,9-Bis((2-fluoro-4-pyridinyl)methyl)-2-hydroxy-9H-fluorene m.p. 200°–201° C. MS (NH$_3$/CI) m/e 401 (M+H); Analysis calc'd for C$_{25}$H$_{18}$F$_2$N$_2$O•0.25H$_2$O: C, 74.15; H, 4.61; N, 6.92; F, 9.38; found: C, 73.91; H, 5.10; N, 6.39; F, 8.94. 49% yield.

EXAMPLE 62

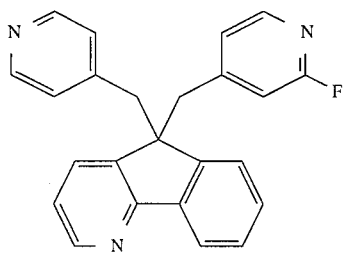

5-(2-Fluoro-4-pyridinyl)methyl)-5-(4-pyridinylmethyl)-5H-indeno[1,2-b]pyridine mp 164°–5° C. MS (NH$_3$/CI) m/e 368 (M+H). Analysis calc'd for C$_{24}$H$_{18}$FN$_3$•0.25 H$_2$O: C, 77.50; H, 5.01; N, 11.30. Found: C, 77.63; H, 4.85; N, 11.20. 22% yield

EXAMPLE 63

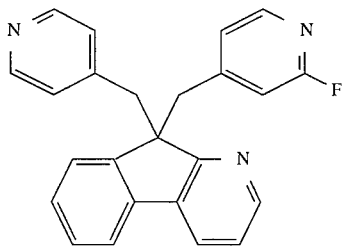

5-(2-Fluoro-4-pyridinyl)methyl)-5-(4-pyridinylmethyl)-5H-indeno[2,1-b]pyridine mp 163°–4° C. MS (NH$_3$/CI) m/e 368 (M+H). Analysis calc'd for C$_{24}$H$_{18}$FN$_3$: C, 78.44; H, 4.94; N, 11.11. Found: C, 78.10; H, 4.78; N, 11.36. 22% yield.

EXAMPLE 64

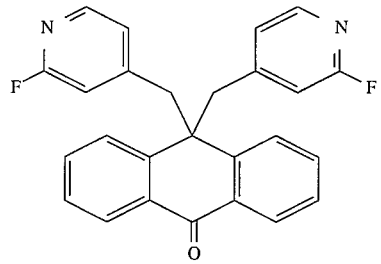

10,10-Bis((2-fluoro-4-pyridinyl)methyl)-9(10H)-anthracenone m.p. 156°–157° C. MS (NH$_3$/CI) m/e 413 (M+H). Analysis calc'd for C$_{26}$H$_{18}$F$_2$N$_2$•0.25 H$_2$O: C, 75.72; H, 4.40; N, 6.70; F, 9.21; found: C, 75.54; H, 4.38; N, 6.76; F, 9.27. 44% yield.

EXAMPLE 65

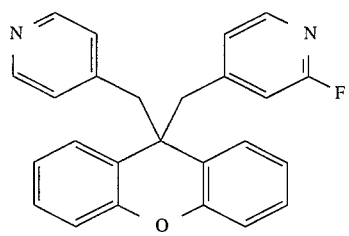

9-((2-Fluoro-4-pyridinyl)methyl)-9-(4-pyridinylmethyl)-9H-xanthene m.p. 180°–1° C. MS (NH$_3$-CI) m/e 383 (M+H). Analysis calc'd for C$_{25}$H$_{19}$FN$_2$O•0.25H$_2$O: C, 77.60; H, 5.08; N, 7.24; found: C, 77.94; H, 4.97; N, 7.25. 3% yield.

EXAMPLE 66

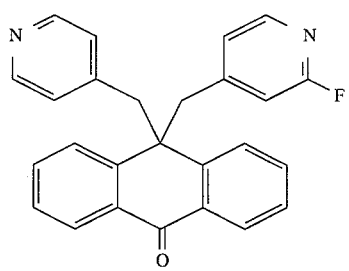

9-((2-Fluoro-4-pyridinyl)methyl)-9-(4-pyridinylmethyl)-9H-xanthene m.p. 199°–201° C. MS (NH$_3$-CI) m/e 395 (M+H). Analysis calc'd for C$_{26}$H$_{19}$FN$_2$O: C, 79.17; H, 4.86; N, 7.10; found: C, 78.84; H, 4.80; N, 7.13. 12% yield.

EXAMPLE 67

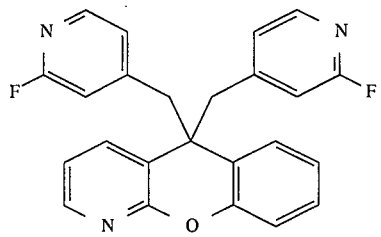

9,9-Bis((2-fluoro-4-pyridinyl)methyl)-4-azaxanthene m.p. 185°–189° C. MS (NH$_3$-CI) m/e 402 (M+H). Analysis calc'd for C$_{24}$H$_{17}$N$_3$F$_2$O: C, 71.81; H, 4.27; N, 10.47; found: C, 71.50; H, 4.25; N, 10.28. 10% yield.

EXAMPLE 68

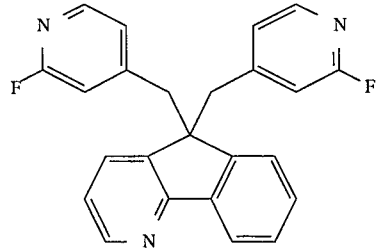

5,5-Bis((2-fluoro-4-pyridinyl)methyl)-5H-indeno[1,2-b]pyridine m.p. 137°–40° C. MS (CI/NH$_3$) m/e 386 (M+H). Analysis calc'd for C$_{24}$H$_{17}$N$_3$F$_2$: C, 74.79; H, 4.45; N, 10.90; F, 9.86; found: C, 74.39; H, 4.51; N, 10.91; F, 9.91. 46% yield.

EXAMPLE 69

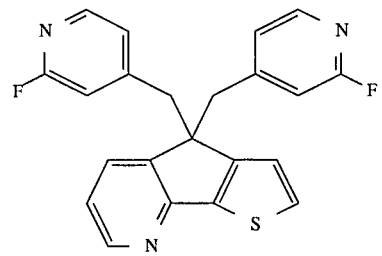

4,4-Bis((2-fluoro-4-pyridinyl)methyl)-4H-thieno[3',2':4,5]cyclopenta[1,2-b]pyridine m.p. 157°–9° C. MS (CI/NH$_3$) m/e 392 (M+H). Analysis calc'd for C$_{22}$H$_{15}$F$_2$N$_3$S: C, 67.50; H, 3.86; N, 10.73; S, 8.19; found: C, 67.11; H, 3.88; N, 10.69; S, 8.34. 55% yield.

EXAMPLE 70

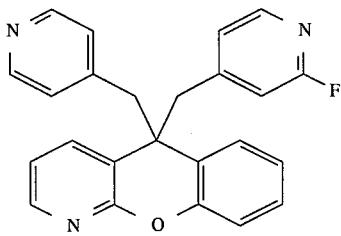

9-((2-Fluoro-4-pyridinyl)methyl)-9-(4-pyridinylmethyl)-4-azaxanthene m.p. 206°–208° C. MS (NH$_3$-CI) m/e 384 (M+H). Analysis calc'd for C$_{24}$H$_{18}$FN$_3$•0.25H$_2$O: C, 74.31; H, 4.81; N, 10.83; found: C, 74.17; H, 4.69; N, 10.67. 12% yield.

EXAMPLE 71

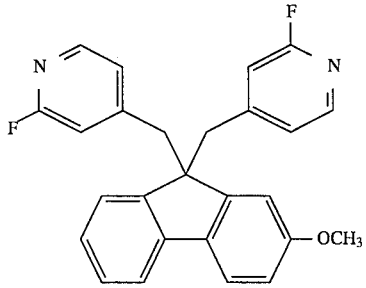

9,9-Bis((2-fluoro-4-pyridinyl)methyl)-2-methoxyfluorene m.p. 143°–146° C. MS (NH$_3$-CI) m/e 415 (M+H). Analysis calc'd for C$_{26}$H$_{20}$F$_2$N$_2$O: C, 75.35; H, 4.86; N, 6.76; found: C, 75.33; H, 4.78; N, 6.67. 54% yield.

EXAMPLE 72

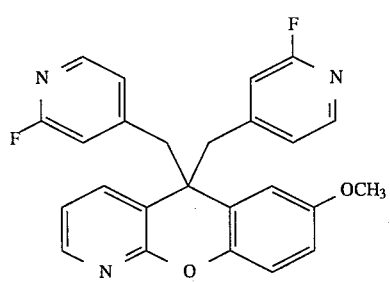

9,9-Bis((2-fluoro-4-pyridinyl)methyl)-7-methoxy-4-azaxanthene m.p. 196°–197° C. MS (NH$_3$-CI) m/e 432 (M+H). Analysis calc'd for C$_{25}$H$_{19}$F$_2$N$_3$O$_2$: C, 69.60; H, 4.44; N, 9.74; found: C, 69.55; H, 4.37; N, 9.74. 8% yield.

EXAMPLE 73

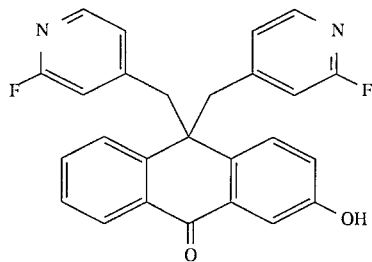

10,10-Bis((2-fluoro-4-pyridinyl)methyl)-3-hydroxy-9(10H)-anthracenone m.p. 219°–221° C. MS (NH$_3$-CI) m/e 429 (M+H); Analysis calc'd for C$_{26}$H$_{18}$F$_2$N$_2$O$_2$: C, 72.89; H, 4.23; N, 6.54; found: C, 72.97; H, 4.19; N, 6.48. 26% yield.

EXAMPLE 74

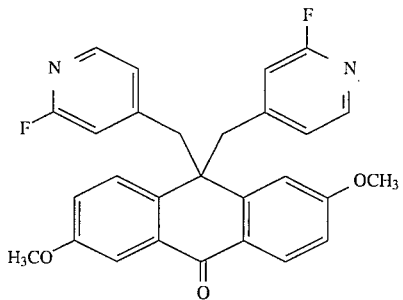

10,10-Bis((2-fluoro-4-pyridinyl)methyl)-2,6-dimethoxy-9(10H)-anthracenone m.p. 151°–2° C. MS (CI/NH$_3$) m/e 473 (M+H). Analysis calc'd for C$_{28}$H$_{22}$F$_2$N$_2$O$_2$: C, 71.17; H, 4.69; N, 5.93; F, 8.04; found: C, 70.76; H, 4.86; N, 5.90; F, 7.91. 12% yield.

EXAMPLE 75

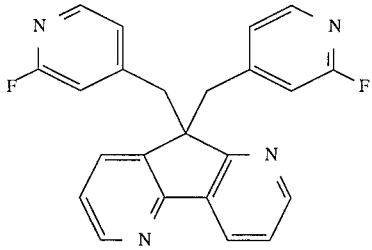

9,9-Bis((2-fluoro-4-pyridinyl)methyl)-cyclopenta[1,2-b:3,4-b']dipyridine m.p. 134°–5° C. MS (CI/NH$_3$) m/e 387 (M+H). Analysis calc'd for C$_{23}$H$_{16}$F$_2$N$_4$: C, 71.49; H, 4.17; N, 14.50; F, 9.83; found: C, 71.08; H, 4.00; N, 14.29; F, 9.96. 27% yield.

EXAMPLE 76

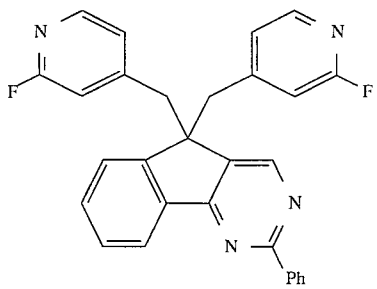

5,5-Bis((2-fluoro-4-pyridinyl)methyl)-2-phenyl-5H-indeno[1,2-d]pyrimidine m.p. 213°–5° C. MS (CI/NH$_3$) m/e 463 (M+H). Analysis calc'd for C$_{29}$H$_{20}$F$_2$N$_4$: C, 75.31; H, 4.36; N, 12.11; F, 8.22; found: C, 74.98; H, 4.31; N, 12.01; F, 8.36. 30% yield.

EXAMPLE 77

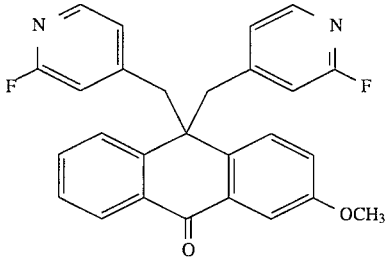

10,10-Bis((2-fluoro-4-pyridinyl)methyl)-3-methoxy-9(10H)-anthracenone m.p. 155°–7° C. MS (CI/NH$_3$) m/e 443 (M+H). Analysis calc'd for C$_{27}$H$_{20}$F$_2$N$_2$O$_2$: C, 73.29; H, 4.56; N, 6.33; F, 8.59; found: C, 72.90; H, 4.54; N, 6.24; F, 8.55. 27% yield.

EXAMPLE 78

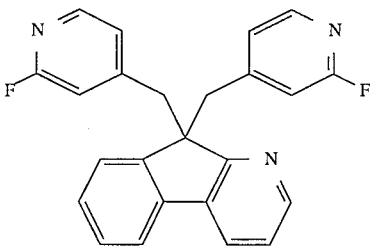

9,9-Bis((2-fluoro-4-pyridinyl)methyl)-9H-indeno-[2,1-b]pyridine m.p. 128°–30° C. MS (CI/NH$_3$) m/e 386 (M+H). Analysis calc'd for C$_{24}$H$_{17}$F$_2$N$_3$: C, 74.79; H, 4.45; N, 10.90; F, 9.86; found: C, 74.50; H, 4.24; N, 10.75; F, 9.87. 35% yield.

EXAMPLE 79

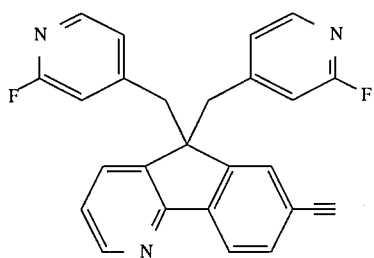

5,5-Bis((2-fluoro-4-pyridinyl)methyl)-7-(ethynyl)-5H-indeno-[1,2-b]pyridine m.p. 139°–40° C. MS (Cl/NH$_3$) m/e 410 (M+H). Analysis calc'd for C$_{26}$H$_{17}$F$_2$N$_3$: C, 76.27; H, 4.19; N, 10.26; F, 9.28; found: C, 75.95; H, 4.14; N, 10.09; F, 9.18. 43% yield.

EXAMPLE 80

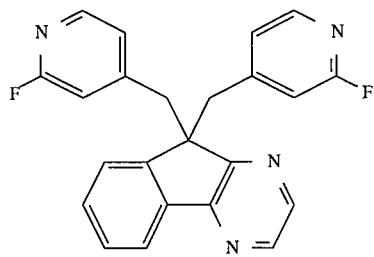

9,9-Bis((2-fluoro-4-pyridinyl)methyl)-9H-indeno-[1,2-b]pyrazine m.p. 119°–20° C. MS (Cl/NH$_3$) m/e 387 (M+H); Analysis calc'd for C$_{23}$H$_{16}$F$_2$N$_2$: C, 71.49; H, 4.17; N, 14.50; F, 9.83; found: C, 71.28; H, 4.12; N, 14.47; F, 9.73. 68% yield.

EXAMPLE 81

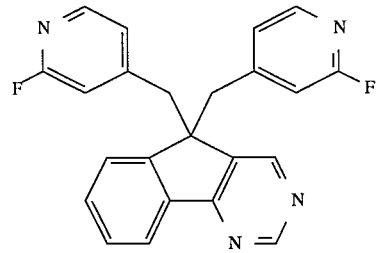

5,5-Bis((2-fluoro-4-pyridinyl)methyl)-5H-indeno-[1,2-d]pyrimidine m.p. 171°–4° C. MS (Cl/NH$_3$) m/e 387 (M+H). Analysis calc'd for C$_{23}$H$_{16}$F$_2$N$_4$: C, 71.49; H, 4.17; N, 14.50; F, 9.83; found: C, 71.30; H, 4.09; N, 14.40; F, 9.96. 64% yield.

EXAMPLE 82

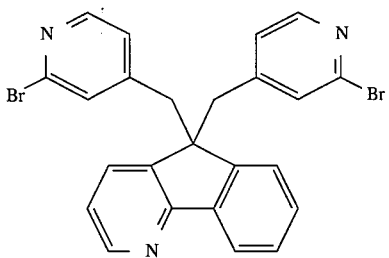

5,5-Bis((2-bromo-4-pyridinyl)methyl)-5H-indeno-[1,2-b]pyridine m.p. 190° C. MS (Cl/NH$_3$) m/e 508 (M+H). Analysis calc'd for C$_{24}$H$_{17}$Br2N$_3$: C, 56.83; H, 3.38; N, 8.28; Br, 31.51; found: C, 57.20; H, 3.43; N, 8.20; Br, 31.12. 63% yield.

EXAMPLE 83

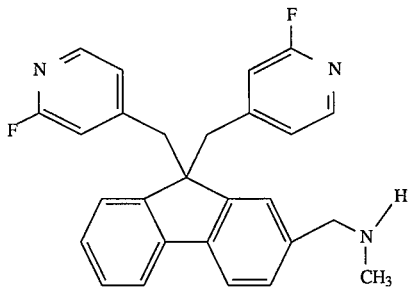

9,9-Bis((2-fluoro-4-pyridinyl)methyl)-2-((N-methylamino)methyl)fluorene m.p. 130°–4° C. MS (Cl/NH$_3$) m/e 428 (M+H). 92% yield.

EXAMPLE 84

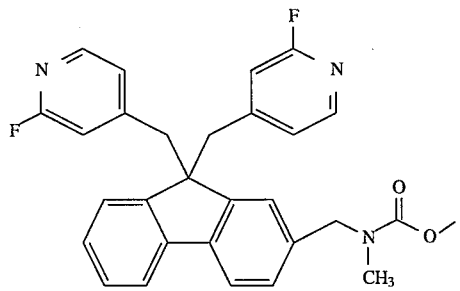

9,9-Bis((2-fluoro-4-pyridinyl)methyl)-2-((N-methyl-N-methoxycarbonylamino)methyl)fluorene oil. MS (Cl/NH$_3$) m/e 486 (M+H). Analysis calc'd for C$_{29}$H$_{25}$F$_2$N$_3$O$_2$·0.5 H$_2$O: C, 70.43; H, 5.30; N, 8.50; found: C, 70.65; H, 5.08; N, 8.53. 85% yield.

EXAMPLE 85

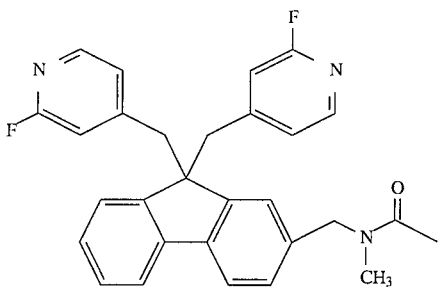

9,9-Bis((2-fluoro-4-pyridinyl)methyl)-2-((N-methyl-N-acetylamino)methyl)fluorene m.p. 136°–7° C. MS (CI/NH$_3$) m/e 470 (M+H); Analysis calc'd for C$_{29}$H$_{25}$F$_2$N$_3$O•0.25H$_2$O: C, 73.48; H, 5.42; N, 8.86; found: C, 73.30; H, 5.34; N, 8.67. 79% yield.

EXAMPLE 86

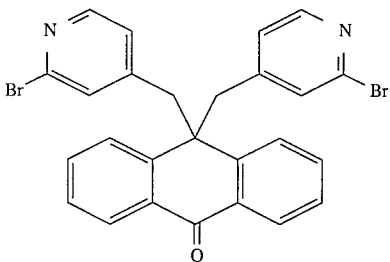

10,10-Bis((2-bromo-4-pyridinyl)methyl)-9(10H)-anthracenone m.p. 182°–3° C. MS (CI/NH$_3$) m/e 535 (M+H). Analysis calc'd for C$_{26}$H$_{18}$Br$_2$N$_2$O: C, 58.45; H, 3.40; N, 5.24; Br, 29.91; found: C, 58.69; H, 3.26; N, 5.22; Br, 29.68. 54% yield.

EXAMPLE 87

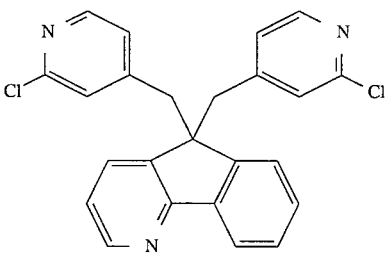

5,5-Bis((2-chloro-4-pyridinyl)methyl)-5H-indeno-[1,2-b]pyridine m.p. 188°–90° C. MS (CI/NH$_3$) m/e 418 (M+H). Analysis calc'd for C$_{24}$H$_{17}$Cl$_2$N$_3$: C, 68.91; H, 4.10; N, 10.04; Cl, 16.95; found: C, 68.70; H, 3.99; N, 9.95; Cl, 16.76. 48% yield.

EXAMPLE 88

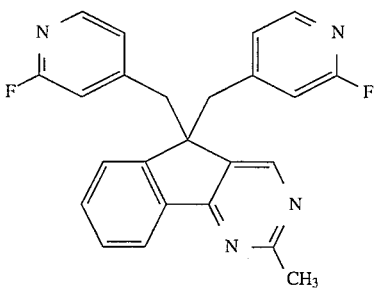

5,5-Bis((2-fluoro-4-pyridinyl)methyl)-2-methyl-5H-indeno-[1,2-d]pyrimidine m.p. 114°–5° C. MS (CI/NH$_3$) m/e 401 (M+H). Analysis calc'd for C$_{24}$H$_{18}$F$_2$N$_4$: C, 71.99; H, 4.53; N, 13.99; F, 9.49; found: C, 71.88; H, 4.52; N, 13; F, 9.87. 31% yield.

EXAMPLE 89

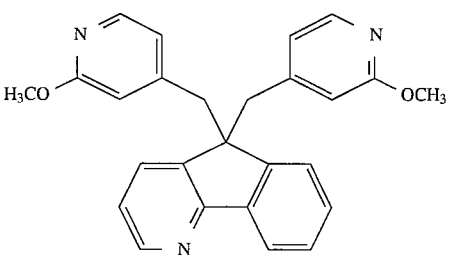

5,5-Bis((2-methoxy-4-pyridinyl)methyl)-5H-indeno-[1,2-b]pyridine m.p. 138°–40° C. MS (CI/NH$_3$) m/e 410 (M+H); Analysis calc'd for C$_{26}$H$_{23}$N$_3$O$_2$: C, 76.26; H, 5.66; N, 10.26; found: C, 75.84; H, 5.54; N, 10.14. 50% yield.

EXAMPLE 90

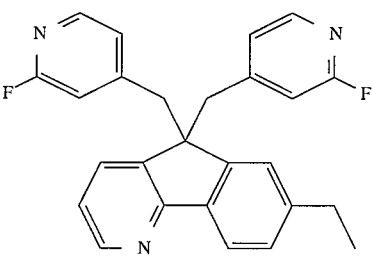

5,5-Bis((2-fluoro-4-pyridinyl)methyl)-7-(ethyl)-5H-indeno-[1,2-b]pyridine

Oil. MS (CI/NH$_3$) m/e 414 (M+H). Analysis calc'd for C$_{26}$H$_{21}$F$_2$N$_3$: C, 75.53; H, 5.12; N, 10.16; found: C, 75; H, 5.36; N, 9.95. 90% yield.

EXAMPLE 91

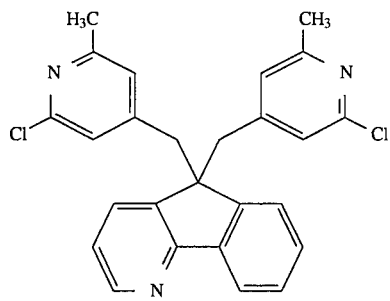

5,5-Bis((2-chloro-6-methyl-4-pyridinyl)methyl)-
5H-indeno-[1,2-b]pyridine m.p. 159°–60° C. MS (CI/NH$_3$) m/e 446 (M+H). Analysis calc'd for C$_{26}$H$_{21}$Cl$_2$N$_3$: C, 69.96; 4.74, 4.68; N, 9.41; Cl, 15.88; found: C, 70.00; 4.74,; N, 9.31; Cl, 15.82. 14% yield.

EXAMPLE 92

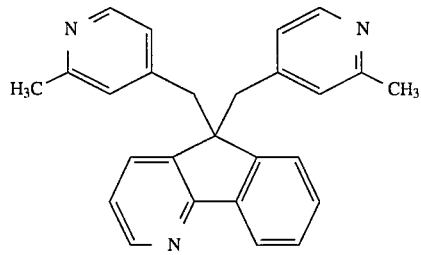

5,5-Bis((2-methyl-4-pyridinyl)methyl)-
5H-indeno-[1,2-b]pyridine m.p. 177°–9° C. MS (CI/NH$_3$) m/e 378 (M+H); Analysis calc'd for C$_{26}$H$_{23}$N$_3$: C, 82.73; H, 6.14; N, 11.13; found: C, 82.54; H, 6.12; N, 11.10. 90% yield.

EXAMPLE 93

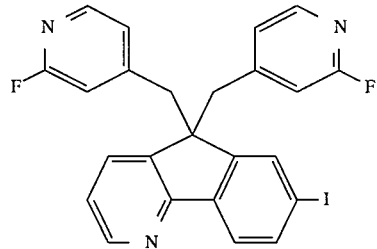

5,5-Bis((2-fluoro-4-pyridinyl)methyl)-7-(iodo)-
5H-indeno-[1,2-b]pyridine m.p. 158°–61° C. MS (CI/NH$_3$) m/e 512 (M+H); Analysis calc'd for C$_{24}$H$_{16}$F$_2$IN$_3$: C, 56.38; H, 3.15; F, 7.43; N, 8.22; found: C, 56.83; H, 3.17; F, 7.58; N, 8.17. 25% yield.

EXAMPLE 94

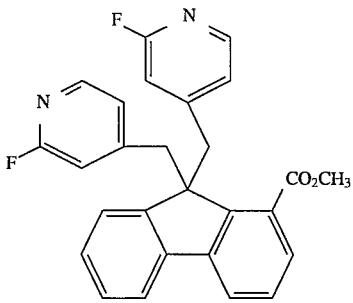

9,9-Bis((2-fluoro-4-pyridinyl)methyl)-
9H-fluorene-1-carboxylic acid, methyl ester m.p. 126°–127° C. MS (NH$_3$/CI) m/e 443 (M+H); Analysis calc'd for C$_{27}$H$_{20}$F$_2$N$_2$O$_2$: C, 73.29; H, 4.56; N, 6.33; F, 8.59; found: C, 72.99; H, 4.56; N, 6.24; F, 8.59. 49% yield.

EXAMPLE 95

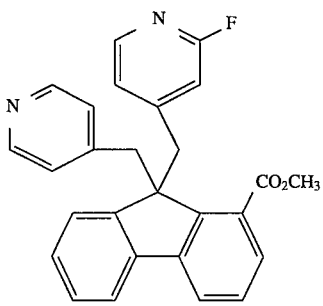

9-((2-Fluoro-4-pyridinyl)methyl)-9-(4-
pyridinylmethyl)-9H-fluorene-1-carboxylic acid,
methyl ester, racemic mp 144°–6° C. MS (NH$_3$/CI) m/e 425 (M+H). Analysis calc'd for C$_{27}$H$_{21}$FN$_2$O$_2$•0.25 H$_2$O: C, 75.60; H, 5.05; N, 6.53; F, 4.43. Found: C, 75.69; H, 4.85; N, 6.42; F, 4.26. 55% yield.

EXAMPLE 96

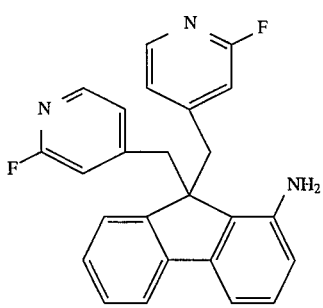

9,9-Bis((2-fluoro-4-pyridinyl)methyl)-
9H-fluoren-1-amine mp 182°–4° C. MS (NH$_3$/CI) m/e 400 (M+H). Analysis calc'd for C$_{25}$H$_{19}$F$_2$N$_3$•0.25 H$_2$O: C, 74.34; H, 4.87; N, 10.40; F, 9.41. Found: C, 74.43; H, 4.68; N, 10.37; F, 9.39. 25% yield.

EXAMPLE 97

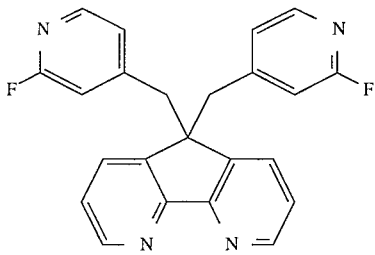

5,5-Bis((2-fluoro-4-pyridinyl)methyl)-5H-cyclopenta[2,1-b:3,4-b']dipyridine m.p. 239°–241° C. MS (NH$_3$/CI) m/e 387 (M+H). Analysis calc'd for C$_{23}$H$_{16}$F$_2$N$_4$•0.25 H$_2$O: C, 70.67; H, 4.25; N, 14.33; F, 9.72; found: C, 70.95; H, 4.05; N, 14.24; F, 9.37. 44% yield.

EXAMPLE 98

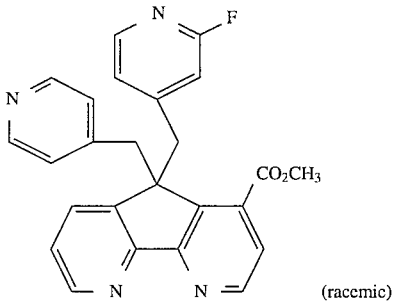

(racemic)

5-((2-Fluoro-4-pyridinyl)methyl)-5-(4-pyridinylmethyl)-5H-cyclopenta[2,1-b:3,4-b'] dipyridine-4-carboxylic acid, methyl ester, dihydrochloride salt (racemic)

m.p. 181°–9° C. MS (NH$_3$-CI) m/e 427 (M+H). Analysis calc'd for C$_{25}$H$_{19}$FN$_4$O$_2$•2HCl•H$_2$O: C, 58.04; H, 4.48; N, 10.83; Cl, 13.70; found: C, 58.45; H, 4.30; N, 10.76; Cl, 13.73. 79% yield.

EXAMPLE 99

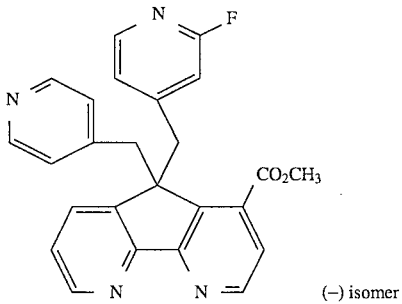

(−) isomer 5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (−)-isomer m.p.-hygroscopic. [α]$_D^{25}$=−14.95° (c=0.6, CHCl$_3$). MS (NH$_3$-CI) m/e 427 (M+H). Analysis calc'd for C$_{25}$H$_{19}$FN$_4$O$_2$•HCl•0.5 H$_2$O: C, 63.63; H, 4.49; N, 11.87; Cl, 7.51; found: C, 63.47; H, 4.06; N, 11.73; Cl, 7.26. 73% yield.

EXAMPLE 100

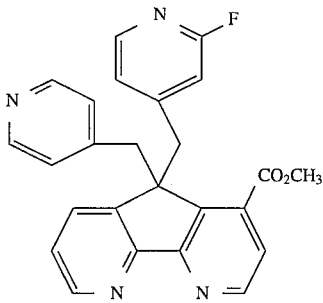

(+) isomer 5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (+)-isomer m.p.-hygroscopic. [α]$_D^{25}$=+14.29° (c=0.6, CHCl$_3$). MS (NH$_3$-CI) m/e 427 (M+H). Analysis calc'd for C$_{25}$H$_{19}$FN$_4$O$_2$•HCl•0.5 H$_2$O: C, 63.63; H, 4.49; N, 11.87; Cl, 7.51; found: C, 63.60; H, 4.03; N, 11.80; Cl, 7.01. 90% yield.

EXAMPLE 101

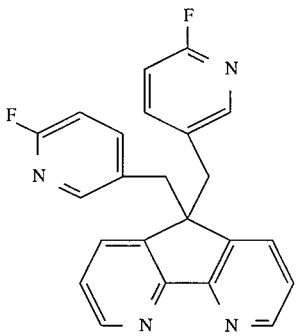

5-((2-Fluoro-4-pyridinyl)methyl)-5-(4-pyridinylmethyl)-5H-cyclopenta[2,1-b:3,4-b']dipyridine-4-carboxylic acid, methyl ester, hydrochloride salt, (+)-isomer m.p. 237°–238° C. MS (NH$_3$-CI) m/e 387 (M+H). Analysis calc'd for C$_{23}$H$_{16}$N$_4$F$_2$•0.25 H$_2$O: C, 70.67; H, 4.25; N, 14.33; F, 9.72; found: C, 70.81; H, 4.4.08; N, 14.26; F, 9.70. 88% yield.

EXAMPLE 102

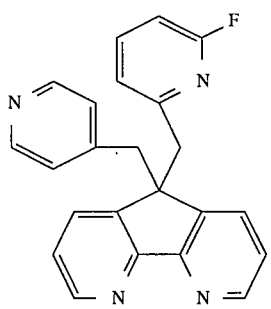

5-((6-Fluoro-2-pyridinyl)methyl)-5-(4-pyridinylmethyl)-5H-cyclopenta[2,1-b:3,4-b']dipyridine m.p. 180°–182° C. MS (NH$_3$-CI) m/e 369 (M+H). Analysis calc'd for C$_{23}$H$_{17}$N$_4$F•0.25 H$_2$O: C, 74.08; H, 4.73; N, 15.02; F, 5.09; found: C, 73.94; H, 4.53; N, 14.93; F, 4.84. 81% yield.

EXAMPLE 103

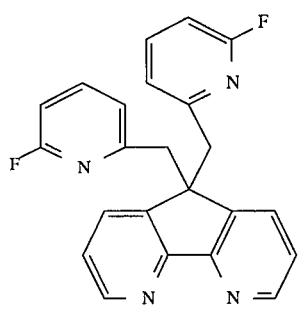

5,5-Bis((6-fluoro-2-pyridinyl)methyl)-5H-cyclopenta[2,1-b:3,4-b']dipyridine m.p. 221°–225° C. MS (NH$_3$-CI) m/e 387 (M+H). Analysis calc'd for C$_{23}$H$_{16}$N$_4$F$_2$•0.33 H$_2$O: C, 70.40; H, 4.28; N, 14.28; F, 9.68; found: C, 70.71; H, 4.04; N, 14.30; F, 9.53. 81% yield.

EXAMPLE 104

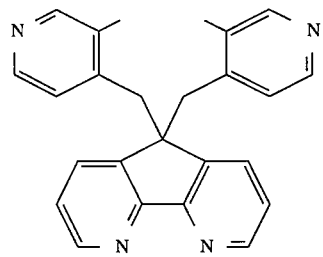

5,5-Bis((3-methyl-4-pyridinyl)methyl)-5H-cyclopenta[2,1-b:3,4-b']dipyridine, trihydrochloride salt m.p. 301° C. (dec). MS (NH$_3$-CI) m/e 379 (M+H). Analysis calc'd for C$_{25}$H$_{22}$N$_4$•3 HCl•1.2 H$_2$O: C, 57.32; H, 5.58; N, 10.69; Cl, 20.30; found: C, 57.68; H, 5.41; N, 9.96; Cl, 20.76. 71% yield.

EXAMPLE 105

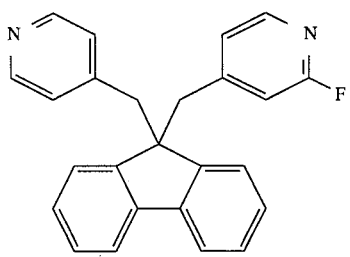

2-Fluoro-4-((9-(4-pyridinylmethyl)-9H-fluoren-9-yl)methyl)pyridine, hydrochloride salt m.p. >220° C. MS (CI/NH$_3$) m/e 386 (M+H). Analysis calc'd for C$_{25}$H$_{21}$N$_2$F•1.2 HCl•0.5 H$_2$O: C, 71.63; H, 5.10; N, 6.68; F, 4.53; Cl, 10.15; found: C, 71.40; H, 4.86; N, 6.54; F, 4.14; Cl, 10.55. 13% yield.

EXAMPLE 106

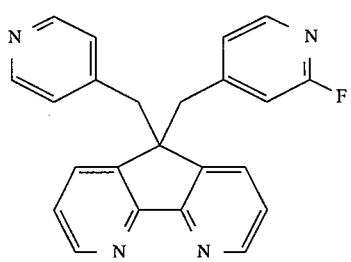

5-((2-Fluoro-4-pyridinyl)methyl)-5-(4-pyridinylmethyl)-5H-cyclopenta[2,1-b:3,4-b']dipyridine m.p. 228°–230° C. MS (CI/NH$_3$) m/e 369 (M+H). Analysis calc'd for C$_{23}$H$_{17}$FN$_4$•0.25 H$_2$O: C, 74.08; H, 4.73; N, 15.02; found: C, 74.25; H, 4.53; N, 15.11. 69% yield.

EXAMPLE 107

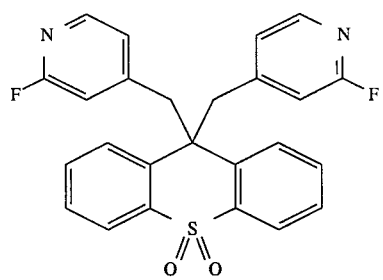

5,5-Bis-(2-fluoropyridin-4-ylmethyl)thioxanthene-10,10-dioxide

A mixture of thioxanthene-10,10-dioxide (1.00 g, 4.3 mmol), 4-chloromethyl-2-fluoropyridine (1.45 g, 9.6 mmol), benzyltriethyl ammonium chloride (90 mg, 0.4 mmol), and a 50% NaOH solution (2.5 mL) in toluene (60 mL) was stirred at 50°–60° C. (internal temperature) for 18 h. After being cooled to ambient temperature, the reaction mixture was poured onto water (100 mL) and extracted three times with ethyl acetate. The combined organic layers were dried over MgSO$_4$, filtered and concentrated in vacuo. Column chromatography (ether:hexanes::1:1) afforded the title product (0.68 g, R$_f$ 0.2): mp >200° C.; NMR (300 MHz, CDCl$_3$): δ 8.3 (d, 2H, J=7), 7.9 (d, 2H, J=7), 7.6 (t, 2H, J=7), 7.45 (t, 2H, J=7), 7.25 (d, 2H, J=7) 6.45–6.35 (m, 2H), 6.2 (s, 2H), 3.8 (s, 4H); CI-HRMS: calcd for C$_{25}$H$_{18}$F$_2$N$_2$O$_2$S: 449.1135 (M+H); found: 449.1150.

EXAMPLE 108

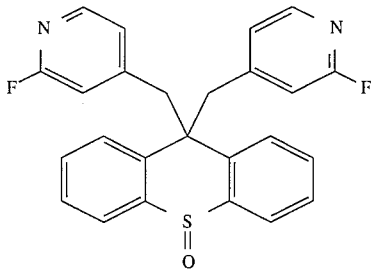

5,5-Bis(2-fluoropyridin-4-ylmethyl) thioxanthene-10-oxide

A mixture of thioxanthene-10-oxide (1.00 g, 4.7 mmol), 4-chloromethyl-2-fluoropyridine (1.73 g, 10.3 mmol), benzyltriethyl ammonium chloride (90 mg, 0.4 mmol), and a 50% NaOH solution (2.5 mL) in toluene (60 mL) was stirred at 50°–60° C. (internal temperature) for 18 h. After being cooled to ambient temperature, the reaction mixture was poured onto water (100 mL) and extracted three times with ethyl acetate. The combined organic layers were dried over MgSO$_4$, filtered and concentrated in vacuo. Column chromatography (ether:hexanes 1:1), followed by preparative TLC, afforded the title product (contaminated with 5,5-bis-(2-fluoropyridin-4-ylmethyl)-thioxanthene-10,10-dioxide) (0.12 g, R$_f$ 0.1): mp >200° C.; NMR (300 MHz, CDCl3): δ8.3 (d, 1H, J=7), 8.2 (d, 2H, J=7), 7.9 (d, 1H, J=7), 7.85 (d, 2H, J=7), 7.6 (t, 2H, J=7), 7.5 (t, 1H, J=7), 7.45 (t, 1H, J=7), 7.35 (t, 2H, J=7),7.25 (d, 1H, J=7), 7.15 (d, 2H, J=7), 6.45–6.35 (m, 2H), 6.2 (s, 2H), 3.9 (s, 2H), 3.8 (s, 2H), 3.15 (s, 2H); CI-MS: 433 (M+H).

EXAMPLE 109

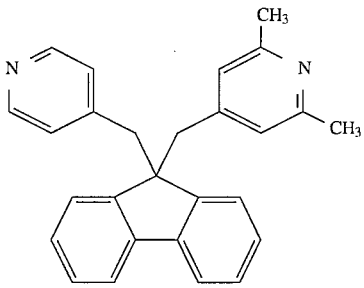

2,6-Dimethyl-4-((9-(4-pyridinylmethyl)-9H-fluoren-9-yl)methyl)pyridine dihydrochloride salt m.p. 180° C. MS (CI/NH$_3$) m/e 372 (M+H for free base). $^1$H NMR (300 MHz, CDCl$_3$) δ: 8.05 (d, 2H), 7.45 (d, 2H), 7.38 (d, 2H), 7.30 (m, 4H), 6.45 (d, 2H), 6.20 (s, 2H), 3.40 (s, 2H), 3.25 (s, 2H), 2.20 (s, 6H). 91% yield (for free base).

EXAMPLE 110

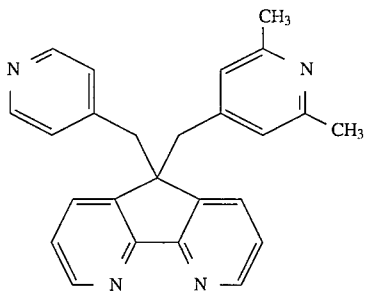

5-((2,6-Dimethyl-4-pyridinyl)methyl)-5-(4-pyridinylmethyl)-5H-cyclopenta[2,1-b:3,4-b']dipyridine m.p. >240° C. MS (CI/NH$_3$) m/e 378 (M+H). Analysis calc'd for C$_{25}$H$_{22}$N$_4$•0.25 H$_2$O: C, 78.40; H, 5.92; N, 14.63; found: C, 78.05; H, 5.58; N, 14.32. 73% yield.

EXAMPLE 111

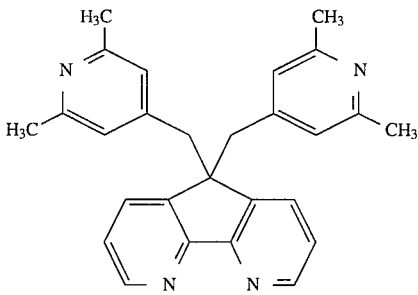

5,5-Bis((2,6-dimethyl-4-pyridinyl)methyl)-5H-cyclopenta[2,1-b:3,4-b']dipyridine, E-2-butendiaote salt m.p. 98°–101° C.(dec). MS (NH$_3$-CI)m/e 407 (M+H). Analysis calc'd for C$_{27}$H$_{26}$N$_4$•C$_4$H$_4$O$_4$•1.2 H$_2$O: C, 67.74; H, 6.05; N, 10.19; found: C, 67.64; H, 6.48; N, 8.71. 50% yield.

EXAMPLE 112

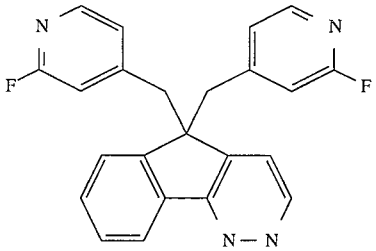

5,5-Bis((2-fluoro-4-pyridinyl)methyl)-5H-indeno[1,2-c]pyridazine m.p. 219°–20° C. (dec.). MS (CI/NH$_3$) m/e 387 (M+H), 278 (M+H-C$_6$H$_4$NF), 169 (M+H)-2(C$_6$H$_4$NF); Analysis calc'd for C$_{23}$H$_{16}$F$_2$N$_4$: C, 71.49; H, 4.17; F, 9.83; N, 14.50; found: C, 71.21; H, 4.13; F, 9.80; N, 14.45. 22% yield.

Although this invention has been described with respect to specific embodiments, the details of these embodiments are not to be construed as limitations. Various equivalents, changes and modifications may be made by one skilled in the art without departing from the spirit and scope of this invention, and it is understood that such equivalent embodiments are part of this invention.

The compounds of Formula (I) possess neurotransmitter release activity and are effective in diminishing memory disruption caused. As such, the compounds of this invention have utility in the treatment of cognitive disorders and/or neurological function deficits and/or mood and mental disturbances in patients suffering from nervous system disorders such as Alzheimer's disease, Parkinson's disease, senile-dementia, multi-infarct dementia, Huntington's disease, mental retardation, Myasthenia Gravis, etc.

The neurotransmitter release activities of the compounds of this invention were determined using standard biochemical assay procedures for example, the neurotransmitter release assay as described below. The ability of compounds of present invention to be effective in diminishing memory disruption is demonstrated in standard behavioral assay procedures for example the rat passive avoidance (PA) hypoxia induced amnesia model as described below.

Neurotransmitter release assay.

The neurotransmitter (Ach) release activities of the compounds of this invention were determined by the assay as described by Nickolson, et al., *Drug Development Research*, (1990) 19: 285–300, a modification of the procedure described by Mulder, et al., *Brain Res.*, (1974) 70: 372.

Male Wistar rats (Charles River) weighing 175–200 grams were used. Rats were decapitated and brains were dissected immediately. Slices (0.3 mm thick) from the parietal cortex were prepared (approximately 100 mg wet weight) and were incubated in 10 ml KrebsRinger medium (KR) containing NaCl (116 mM), KCl (3 mM), $CaCl_2$ (1.3 mM), $MgCl_2$ (1.2 mM), $KH_2PO_4$ (1.2 mM), $Na_2SO_4$ (1.2 mM), $NaHCO_3$ (25.0 mM), and glucose (11.0 mM), to which was added 10 uCi $^3$H-choline (specific activity approximately 35 Ci/mM; NEN) and 10 mM unlabeled choline to give a final concentration of one micromole. The brain preparations were incubated for 30 min. at 37° C. under a steady flow of 95% $O_2$/5% $CO_2$. Under these conditions, part of the radioactive choline taken up by the preparation was converted into radioactive acetylcholine (ACh) by the cholinergic nerve endings stored in synaptic vesicles, and released upon depolarization by high potassium ion (K+) containing media.

After labelling of the ACh stores, the slices were washed three times with non-radioactive KR medium and transferred to a superfusion apparatus to measure the drug effects on ACh release. The superfusion apparatus consisted of 10 thermostated glass columns of 5 mm diameter that were provided with GF/F glass fiber filters to support the slices (approximately 10 mg tissue/column). Superfusion was carried out in KR-medium (0.3 ml/min.) containing 10 mM hemicholine-3 (HC-3). The HC-3 prevents the reuptake of choline formed during the superfusion from phospholipids and released ACh, which would be converted into unlabeled ACh and released in preference to the preformed labeled ACh. The medium was delivered by a 25-channel peristaltic pump (Ismatec by Brinkman) and warmed to 37° C. in a thermostated stainless steel coil before entering the superfusion column. Each column was provided with a 4-way slider valve (Beckmann instruments) which allowed rapid change of low to high K+/KR-medium, and with two 10-channel 3-way valves that were used to change from drug-free to drug-containing low and high K+/KR-medium. After 15 min. of washout of non-specifically bound radioactivity, collection of 4 min. fractions was initiated. After three 4 min. collections, the original medium was changed to a KR-medium in which the KCl concentration had been increased to 25 mM (high K+ medium) (S1). Depolarization-induced stimulation of release by high K+/KR-medium lasted for 4 min. Drug free low and high K+/KR-media were then substituted by drug- and vehicle-containing low- and high-K+/KR-medium, and superfusion was continued for three 4 min. collections with low K+/KR-medium, one 4 min. collection with high K+/KR-medium (s2), and two 4 min. collections with low K+/KR-medium.

Drug was added to the media by 100-fold dilutions of appropriate concentrations of the drug (in 0.9% saline) with either low- or high-K+/KR-medium. For comparative purposes, linopirdine was also run.

All superfusion fractions were collected in liquid scintillation counting vials. After superfusion, the slices were removed from the superfusion columns and extracted with 1.0 ml of 0.1N HCl. Liquiscint (NEN) counting fluid (12 ml) was added to superfusion fractions and extracts, and the samples were counted in a Packard Tricarb Liquid Scintillation Counter. No corrections were made for quenching.

The ratio of s2/S1 (as compared to controls where no drug was present during S2) was a measure of the ability of the drug to enhance or depress stimulus-induced acetylcholine release.

Representative compounds of this invention were tested in the neurotransmitter release assay and found to be effective in causing drug-induced release of neurotransmitters. The results, expressed as % increase of drug-induced Ach release, are shown in Table II below.

Rat Passive Avoidance (PA) Hypoxia Induced Amnesia:

Unfasted male CD rats, weighing between 165–210 grams, were trained in a PA apparatus using the following procedure: rats were placed in the clear side of the two compartment chamber and allowed 90 seconds to enter the dark compartment. Ten seconds after entering the dark chamber, a 3 second footshock (1.0 mA) was applied to the grid floor followed by an additional 10 second delay, and another 3 second footshock was applied. Retentions were tested 4 hours later. The rats were allowed 300 seconds to enter the dark compartment; time was taken. Memory disruption was induced by exposing the rats to a gas mixture containing 6.5% oxygen supplemented with nitrogen for 30 minutes before passive avoidance training. Doses of the test compound were administered (0.1 ml/100 g, SC.) relative to time of PA training.

Representative compounds of this invention were tested in the rat passive avoidance (PA) hypoxia induced amnesia model and found to be effective in diminishing the memory disruption caused by hypoxia (significantly different from vehicle, using a Mann-Whitney U Test). The results, median retention latencies, are shown in Table II and Table III below.

Microdialysis procedure

Male Wistar Rats are anaesthetized and guide cannulas stereotaxically implanted into the brain at the level of the dorsal hippocampus. Following a minimum recovery period of 72 h, dialysis probes (0.5 mm diameter, 4.0 mm long, from BAS) are inserted into the hippocampus through the guide cannulas. The probes are perfused at a rate of 2 μl/min with artificial cerebrospinal fluid containing 100 μM physostigmine sulfate (a cholinesterase inhibitor). Rats are allowed to acclimate for 2 hours prior to sample collection. Dialysate samples are collected every 20 min (40 μl) and immediately injected onto a high performance liquid chromatograph equipped for electrochemical detection (HPLC-EC) of acetylcholine (ACh). Following collection of 3 baseline samples, drugs or vehicle control are administered in 0.01 ml/g body weight and dialysate samples are collected for an additional 3 h. The ACh peak heights of the 3 samples prior to drug administration are averaged together to determine baseline ACh levels. ACh peak heights post drug administration are measured and used to determine percent change over baseline ACh levels. At the end of experiments, probe placement is verified histologically.

HPLC-EC ACh Assay

ACh is separated by reverse phase chromatography (Hamilton PRP-1 column 150×4.5 mm) and converted to acetate, betaine and hydrogen peroxide on an immobilized enzyme reactor column (BAS). Hydrogen peroxide is then detected electrochemically. Mobile phase for the chromatography consists of 0.2M $Na_2HPO_4$, 0.1 mM EDTA, 0.5 mM SOS, 0.9 mM TMA.Cl, with pH adjusted to 8.0 with phosphoric acid and 50 ml Kathon CG (ESA) added to each liter of mobile phase to retard bacterial growth.

Results.

Figure 2:
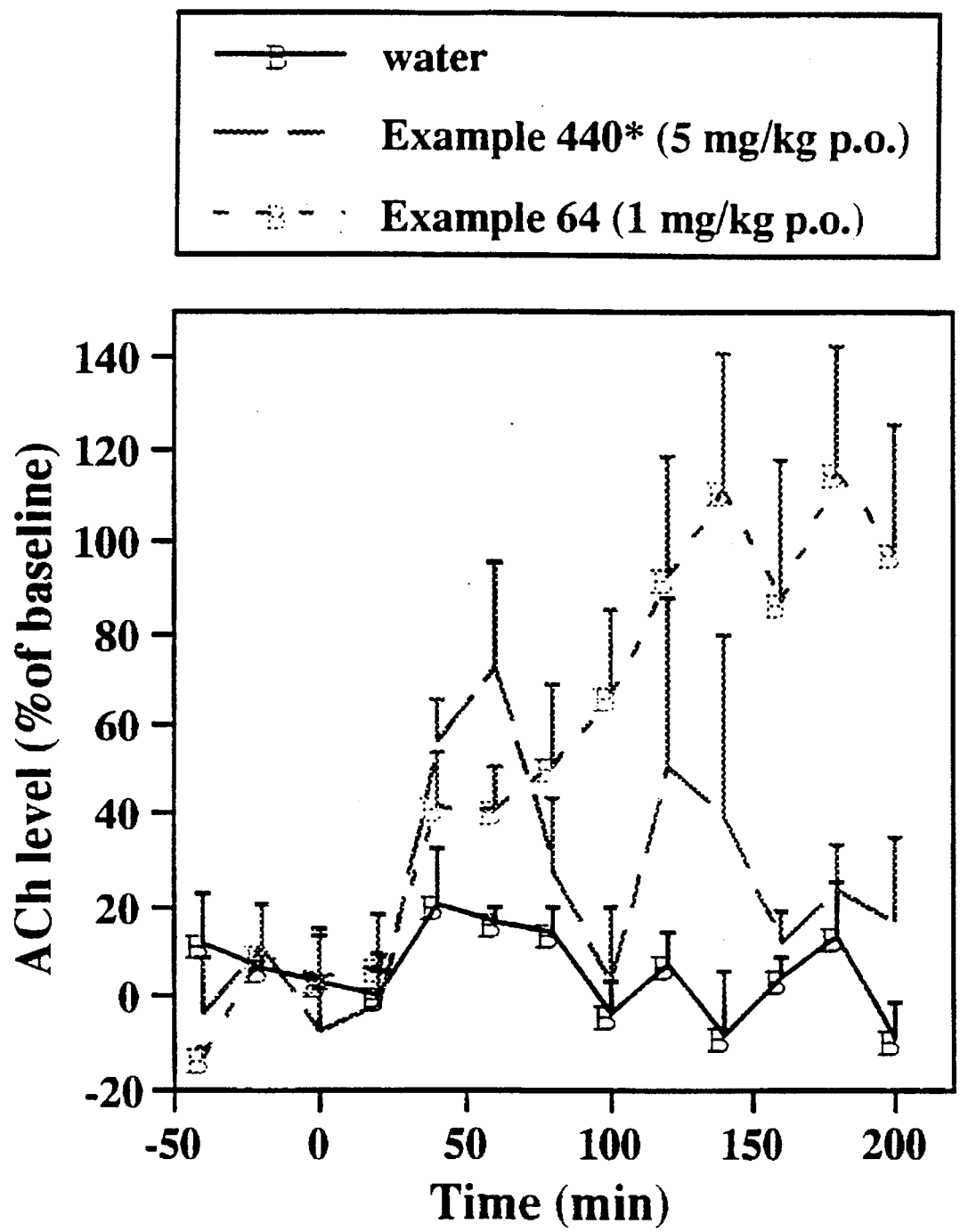

FIGS. 1 and 2 show the effects of fluorine substitution to the pendant groups of the anthrone and azafluorene core series on the ability of compounds to increase the level of ACh in the rat hippocampus in vivo. All compounds were tested at 5 mg/kg except Ex. No 64 which was administered at 1 mg/kg. The compounds were dosed orally except in the case of Ex. No 611 of U.S. Pat. No. 5,173,489 which was given i.p. Ex. No. 611 of U.S. Pat. No. 5,173,489 had no effect on ACh levels over what was observed after vehicle administration (FIG. 1). This was observed even though the compound was administered by a route (i.p.) which should lead to greater bioavailability than the oral route. Example 68 of the present invention, the bis-fluorinated analog of Example 611 or U.S. Pat. No. 5,173,489, on the other hand, led to a 2-fold increase in ACh levels which was maintained for over 1 hour (FIG. 1). The anthrone compound Ex. No. 440 of U.S. Pat. No. 5,173,489, at 5 mg/kg, led to a peak ACh level of 72% over baseline (FIG. 2). Ex. No. 64 of the present invention, which is the bis-fluoro analog of Ex. No. 440 of U.S. Pat. No. 5,173,489, at 1 mg/kg, led to a delayed increase in ACh levels reaching a peak of over 100% above baseline (FIG. 2). In contrast to the observed effects of Example 440 of U.S. Pat. No. 5,173,489, the increase in ACh level after administration of Example 64 of the present invention was maintained for the entire duration of testing (3 hours). Tabular data from all microdialysis test is shown in Table IV.

FIG. 1. Comparison of the effects of *Example 611 of U.S. Pat. No. 5,173,489 to Example 88 of the present invention on ACh levels in the rat hippocampus in vivo.

FIG. 2. Comparison of the effects of *Example 440 of U.S. Pat. No. 5,173,489 to Example 64 of the present invention on ACh levels in the rat hippocampus in vivo.

TABLE II

| Example | Ach Release % @ 10 μM | PA Hypoxia: |
|---|---|---|
| 1 | 92 | |
| 2 | 220 | |
| 3 | 145 | |
| 4 | 146 | |
| 5 | 224 | |
| 6 | 163 | |
| 7 | 439 | |
| 8 | 130 | |
| 10 | 118 | |
| 11 | 757 | |
| 14 | 533 | Active |
| 15 | 348 | |
| linopirdine (Ex No 4 of U.S. Pat. No. .#######) | 408 | Active |

TABLE III

| Ex. No. | ACh Release @ 10 μM | % ACh (cor.) | $EC_{50}$ (uM) |
|---|---|---|---|
| 62 | 317 | 138 | 0.3 |
| 63 | 253 | 40 | |
| 85 | 202 | 39 | |
| 84 | 268 | 65 | |
| 64 | 287 | 111 | 0.66 |
| 65 | 300 | 100 | 0.82 |
| 83 | 127 | 14 | |
| 68 | 466 | 167 | 0.76 |
| 69 | 423 | 140 | 0.65 |
| 66 | 320 | 116 | 0.31 |
| 67 | 403 | 138 | 0.64 |
| 70 | 706 | 223 | 0.35 |
| 71 | 285 | 102 | 1.24 |
| 72 | 338 | 111 | 0.85 |
| 61 | 473 | 174 | |
| 73 | 328 | 118 | |
| 74 | 476 | 207 | 0.88 |
| 75 | 200 | 50 | 1.21 |
| 76 | 239 | 74 | 0.66 |
| 77 | 258 | 90 | 0.66 |
| 86 | 292 | 99 | |
| 82 | 227 | 66 | |
| 79 | 328 | 102 | 2.65 |
| 80 | 323 | 165 | 2.33 |
| 81 | 283 | 105 | 0.64 |
| 94 | 318 | 60 | |
| 95 | 409 | 193 | |
| 96 | 550 | 132 | 0.57 |
| 97 | 290 | 176 | 2.62 |
| 98 | 313 | 104 | |
| 99 | 383 | 139 | |
| 100 | 343 | 119 | |
| 101 | 172 | 35 | |
| 102 | 338 | | |
| 103 | 312 | | |
| 104 | 342 | | |
| 105 | 276 | 138 | |
| 106 | 278 | 118 | |
| 107 | 502 | 176 | |
| 108 | 981 | 385 | |
| 109 | 434 | | |
| 110 | 273 | 135 | |

TABLE IV

| Ex No. | Dose mg/kg (no. tests) | vehicle | AUC | Peak | Duration |
|---|---|---|---|---|---|
| | (7) | water | 36 ± 25 | 24 ± 9 @ 40 | 20 |
| | (14) | methocel | 16 ± 71 | 23 ± 10 @ 60 | NSP |
| Ex. 4 | 5 (5) | water | 83 ± 73 | 50 ± 16 @ 40 | 20 |
| U.S. Pat. No. 4,760,083 | 10 (9) | water | 191 ± 68 | 56 ± 7 @ 40 | 60 |
| | 20 (6) | water | 315 ± 108 | 68 ± 26 @ 100 | 100 |
| | 10 (10) | methocel | 212 ± 61 | 62 ± 15 @ 40 | 100 |
| | 20 (3) | methocel | 600 ± 71 | 117 ± 36 @ 40 | 140 |
| Ex 440 | 5 (4) | water | 44 ± 34 | 18 ± 15 @ 20 | NSP |
| U.S. Pat. No. 5,173,489 | 10 (10) | water | 705 ± 112 | 127 ± 31 @ 60 | 100 |
| 64 | 0.5 (6) | methocel | 253 ± 156 | 40 ± 21 @ 40 | NSP |
| | 1 (4) | methocel | 711 ± 158 | 115 ± 27 @ 180 | > |
| 73 | 5 (3) | methocel | 170 ± 126 | 36 ± 12 @ 20 | NSP |
| Ex 456 | 5 (4) | water | 79 ± 45 | 36 ± 15 @ 20 | NSP |
| U.S. Pat. No. 5,173,489 | 10 (4) | water | 157 ± 108 | 72 ± 30 @ 40 | 40 |
| 71 | 5 (3) | methocel | 126 ± 74 | 34 ± 16 @ 60 | NSP |
| 61 | 5 (3) | methocel | 95 ± 61 | 48 ± 22 @ 20 | 40 |
| 62 | 5 (3) | water | 160 ± 187 | 47 ± 32 @ 40 | NSP |
| | 10 (4) | water | 221 ± 85 | 52 ± 10 @ 20 | >40 |
| 68 | 2 (5) | water | 240 ± 82 | 47 ± 12 @ 40 | |
| | 5 (5) | water | 871 ± 272 | 121 ± 25 @ 100 | 120 |
| | 1 (7) | methocel | 304 ± 88 | 74 ± 29 @ 100 | 120 |
| | 5 (3) | methocel | 942 ± 324 | 201 ± 68 @ 80 | >80 |
| 73 | 5 (3) | methocel | 432 ± 106 | 86 ± 42 @ 60 | 80 |
| 67 | 1 (4) | methocel | 666 ± 212 | 123 ± 62 @ 200 | > |
| | 5 (3) | methocel | 1423 ± 595 | 199 ± 80 @ 160 | > |
| 107 | 5 (5) | methocel | 281 ± 226 | 41 ± 10 @ 20 | NSP |
| 108 | 1 (5) | methocel | 184 ± 124 | 34 ± 19 @ 100 | NSP |
| | 5 (5) | methocel | 799 ± 202 | 108 ± 80 @ 80 | > |
| 76 | 5 (3) | methocel | 96 ± 67 | 39 ± 25 @ 20 | NSP |
| 75 | 5 (3) | methocel | 302 ± 35 | 67 ± 12 @ 20 | 60 |
| 65 | 5 (5) | methocel | 147 ± 69 | 40 ± 11 @ 20 | 60 |
| 7 | 5 (3) | water | 235 ± 87 | 53 ± 19 @ 180 | NSP |
| 69 | 5 (5) | water | 285 ± 40 | 44 ± 14 @ 20 | 40 |
| 72 | 5 (3) | methocel | 138 ± 109 | 34 ± 22 @ 60 | NSP |
| Ex 532 U.S. Pat. No. 5,173,489 | 10 (5) | methocel | 76 ± 88 | 58 ± 22 @ 40 | 40 |
| 97 | 10 (6) | methocel | 649 ± 188 | 102 ± 29 @ 100 | 120 |
| 81 | 5 (6) | methocel | 250 ± 68 | 53 ± 17 @ 60 | 100 |

AUC - Area % under the curve (from graphical Figure).
Peak - maximal % increase of ACh release over baseline @ minutes after administration.
Duration - minutes of release above statistical significance.
NSP - no significant points.

The compounds of this invention may also be used as reagents or standards in the biochemical study of neurological function, dysfunction, and disease.

Dosage and Formulation

Compounds of this invention can be administered to treat cognitive disorders and/or neurological function deficits and/or mood and mental disturbances by any means that produces contact of the active agent with the agent's site of action in the body of a mammal or patient. The compounds can be administered by any conventional means available for use in conjunction with pharmaceuticals either as individual therapeutic agent or in combination of therapeutic agents. They can be administered alone, but are generally administered as a pharmaceutical composition comprised of a compound and a pharmaceutical carrier selected on the basis of the chosen route of administration and standard pharmaceutical practice.

The dosage administered will vary depending on the use and known factors such as the pharmacodynamic character of the particular agent, and its mode and route of administration; the recipient's age, weight, and health; nature and extent of symptoms; kind of concurrent treatment; frequency of treatment; and the desired effect. For use in the treatment of said diseases or conditions, the compounds of this invention can be orally administered daily at a dosage of the active ingredient of 0.001 to 100 mg/kg of body weight. Ordinarily, a dose of 0.01 to 10 mg/kg/day in divided doses one to four times a day, or in sustained release formulation was effective in obtaining the desired pharmacological effect.

Dosage forms (pharmaceutical compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets, and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film coated to mask any unpleasant taste, or used to protect the active ingredients from the atmosphere, or to allow selective disintegration of the tablet in the gastrointestinal tract.

Liquid dosage forms for oral administration can contain coloring and flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Anti-oxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in *"Remington's Pharmaceutical Sciences"*, A. Osol, a standard reference ion this field.

Useful pharmaceutical dosage-forms for administration of the compounds of this invention can be illustrated as follows:

Capsules

A large number of unit capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil was prepared and injected by means of a positive displacement was pumped into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed absorption.

Injectable

A parenteral composition suitable for administration by injection is prepared by dissolving 1.5% by weight of active ingredient in a solution containing 10% by volume of propylene glycol in water. The solution is sterilized by commonly used techniques.

Suspension

An aqueous suspension is prepared for oral administration so that each 5 milliliters contains 25 milligrams of finely divided active ingredients, 200 milligrams of sodium carboxymethyl cellulose, 5 milligrams of sodium benzoate, 1.0 gram of sorbitol solution, U.S.P., and 0.025 milliliter of vanillin.

Nasal Spray

An aqueous solution is prepared such that each 1 milliliter contains 10 milligrams of active ingredient, 1.8 milligrams methylparaben, 0.2 milligram propylparaben and 10 milligrams methylcellulose. The solution is dispensed into 1 milliliter vials.

Lung Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

The foregoing disclosure includes all the information deemed essential to enable those of skill in the art to practice the claimed invention. Because the cited applications may provide further useful information these cited materials are hereby incorporated by reference.

What is claimed is:

1. A compound of the formula:

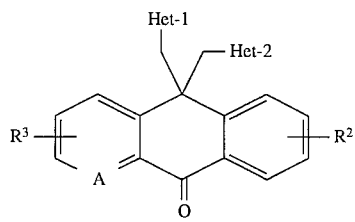

or a pharmaceutically acceptable salt or prodrug thereof, wherein:

A is N or CH;

Het-1 and Het-2 are each independently selected from 2-pyridyl, 3-pyridyl or 4-pyridyl substituted with X $R^2$ and $R^3$ are independently selected from H, F, Cl, Br, I, $CF_3$, $R^4$, or —C≡CH;

$R^4$ is alkyl of 1 to 4 carbons;

X in each instance is independently selected from H, F, Cl, Br, I, or $CF_3$, provided that at least one X is other than H.

2. A compound of claim 1, wherein Het-1 and Het-2 are independently 4-pyridyl substituted with X.

3. A compound of claim 2 wherein A is CH.

4. A compound of claim 3, wherein $R^2$ and $R^3$ are independently H, F, Br, or $CF_3$.

5. A compound of claim 4, wherein one X is H and the other F; and, $R^2$ and $R^3$ are each H.

6. A compound of claim 5 which is 10-((2-Fluoro-4-pyridyl)methyl)-10-(4-pyridylmethyl)-9(10H)-anthracenone.

7. A compound of claim 4, wherein each X is F and $R^2$ and $R^3$ are each H.

8. A compound of claim 7 which is 10,10-Bis((2-fluoro-4-pyridinyl)methyl)-9(10H)-anthracenone.

9. A compound of the formula:

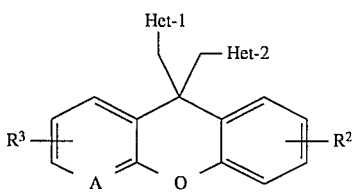

or a pharmaceutically acceptable salt or prodrug thereof wherein:

A is H or CH;

Het-1 and Het-2 are each independently selected from 2-pyridyl, 3-pyridyl or 4-pyridyl substituted with X $R^2$ and $R^3$ are independently selected from H, F, Cl, Br, I, $CF_3$;

X in each instance is independently selected from H, F, Cl, Br, I, or $CF_3$, provided that at least one X is other than H.

10. A compound of claim 9, wherein A is CH;

each of Het-1 and Het-2 is independently 4-pyridyl, substituted with X; and, each X is independently H, F, Cl, or Br.

11. A compound of claim 10 which is 9-((2-Fluoro-4-pyridinyl)methyl)-9-(4-pyridinylmethyl)-9H-xanthene.

12. A compound of claim 9, wherein A is N;

each of Het-1 and Het-2 is independently 4-pyridyl, substituted with X; and, each X is independently H, F, Cl, or Br.

13. A compound of claim 12 which is 9,9-Bis((2-fluoro-4-pyridinyl)methyl)-4-azaxanthene.

14. A compound of the formula:

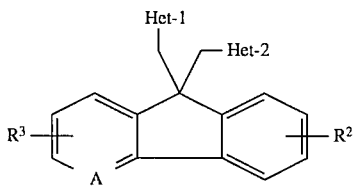

or a pharmaceutically acceptable salt or prodrug thereof wherein:

A is CH or N;

$R^2$ and $R^3$ are each H;

Het-1 and Het-2 are independently selected from 2-pyridyl, 3-pyridyl, or 4-pyridyl, substituted with X;

each X is independently H, F, or Cl provided that at least one X is F or both X's are Cl.

15. A compound of claim 14 which is 5-(2-Fluoro-4-pyridinyl)methyl)-5-(4-pyridinylmethyl)-5H-indeno[1,2-b]pyridine.

16. A compound of claim 14 which is 5,5-Bis((2-fluoro-4-pyridinyl)methyl)-5H-indeno[1,2-b]pyridine.

17. A compound of claim 14 which is 5,5-Bis((2-chloro-4-pyridinyl)methyl)-5H-indeno[1,2-b]pyridine.

18. A pharmaceutical composition comprising a pharmaceutically acceptable carrier and a therapeutically effective amount of a compound of claim 1.

19. A pharmaceutical composition comprising a pharmaceutically acceptable carrier and a therapeutically effective amount of a compound of claim 2.

20. A pharmaceutical composition comprising a pharmaceutically acceptable carrier and a therapeutically effective amount of a compound of claim 3.

21. A pharmaceutical composition comprising a pharmaceutically acceptable carrier and a therapeutically effective amount of a compound of claim 4.

22. A pharmaceutical composition comprising a pharmaceutically acceptable carrier and a therapeutically effective amount of a compound of claim 5.

23. A pharmaceutical composition comprising a pharmaceutically acceptable carrier and a therapeutically effective amount of a compound of claim 6.

24. A pharmaceutical composition comprising a pharmaceutically acceptable carrier and a therapeutically effective amount of a compound of claim 7.

25. A pharmaceutical composition comprising a pharmaceutically acceptable carrier and a therapeutically effective amount of a compound of claim 8.

26. A pharmaceutical composition comprising a pharmaceutically acceptable carrier and a therapeutically effective amount of a compound of claim 9.

27. A pharmaceutical composition comprising a pharmaceutically acceptable carrier and a therapeutically effective amount of a compound of claim 10.

28. A pharmaceutical composition comprising a pharmaceutically acceptable carrier and a therapeutically effective amount of a compound of claim 11.

29. A pharmaceutical composition comprising a pharmaceutically acceptable carrier and a therapeutically effective amount of a compound of claim 12.

30. A pharmaceutical composition comprising a pharmaceutically acceptable carrier and a therapeutically effective amount of a compound of claim 13.

31. A pharmaceutical composition comprising a pharmaceutically acceptable carrier and a therapeutically effective amount of a compound of claim 14.

32. A pharmaceutical composition comprising a pharmaceutically acceptable carrier and a therapeutically effective amount of a compound of claim 15.

33. A pharmaceutical composition comprising a pharmaceutically acceptable carrier and a therapeutically effective amount of a compound of claim 16.

34. A pharmaceutical composition comprising a pharmaceutically acceptable carrier and a therapeutically effective amount of a compound of claim 17.

35. A method for the treatment of cognitive or neurological dysfunction comprising administering to a host in need thereof a therapeutically effective amount of a compound of claim 1.

36. A method for the treatment of cognitive or neurological dysfunction comprising administering to a host in need thereof a therapeutically effective amount of a compound of claim 2.

37. A method for the treatment of cognitive or neurological dysfunction comprising administering to a host in need thereof a therapeutically effective amount of a compound of claim 3.

38. A method for the treatment of cognitive or neurological dysfunction comprising administering to a host in need thereof a therapeutically effective amount of a compound of claim 4.

39. A method for the treatment of cognitive or neurological dysfunction comprising administering to a host in need thereof a therapeutically effective amount of a compound of claim 5.

40. A method for the treatment of cognitive or neurological dysfunction comprising administering to a host in need thereof a therapeutically effective amount of a compound of claim 6.

41. A method for the treatment of cognitive or neurological dysfunction comprising administering to a host in need thereof a therapeutically effective amount of a compound of claim 7.

42. A method for the treatment of cognitive or neurological dysfunction comprising administering to a host in need thereof a therapeutically effective amount of a compound of claim 8.

43. A method for the treatment of cognitive or neurological dysfunction comprising administering to a host in need thereof a therapeutically effective amount of a compound of claim 9.

44. A method for the treatment of cognitive or neurological dysfunction comprising administering to a host in need thereof a therapeutically effective amount of a compound of claim 10.

45. A method for the treatment of cognitive or neurological dysfunction comprising administering to a host in need thereof a therapeutically effective amount of a compound of claim 11.

46. A method for the treatment of cognitive or neurological dysfunction comprising administering to a host in need thereof a therapeutically effective amount of a compound of claim 12.

47. A method for the treatment of cognitive or neurological dysfunction comprising administering to a host in need thereof a therapeutically effective amount of a compound of claim 13.

48. A method for the treatment of cognitive or neurological dysfunction comprising administering to a host in need thereof a therapeutically effective amount of a compound of claim 14.

49. A method for the treatment of cognitive or neurological dysfunction comprising administering to a host in need thereof a therapeutically effective amount of a compound of claim 15.

50. A method for the treatment of cognitive or neurological dysfunction comprising administering to a host in need thereof a therapeutically effective amount of a compound of claim 16.

51. A method for the treatment of cognitive or neurological dysfunction comprising administering to a host in need thereof a therapeutically effective amount of a compound of claim 17.

* * * * *